United States Patent
Little

(10) Patent No.: US 11,557,852 B2
(45) Date of Patent: Jan. 17, 2023

(54) CABLE ASSEMBLY

(71) Applicants: FOXCONN (KUNSHAN) COMPUTER CONNECTOR CO., LTD., Kunshan (CN); FOXCONN INTERCONNECT TECHNOLOGY LIMITED, Grand Cayman (KY)

(72) Inventor: Terrance F. Little, Fullerton, CA (US)

(73) Assignees: FOXCONN (KUNSHAN) COMPUTER CONNECTOR CO., LTD., Kunshan (CN); FOXCONN INTERCONNECT TECHNOLOGY LIMITED, Grand Cayman (KY)

( * ) Notice: Subject to any disclaimer, the term of this patent is extended or adjusted under 35 U.S.C. 154(b) by 502 days.

(21) Appl. No.: 16/701,067

(22) Filed: Dec. 2, 2019

(65) Prior Publication Data

US 2020/0176923 A1 Jun. 4, 2020

Related U.S. Application Data

(60) Provisional application No. 62/899,156, filed on Sep. 12, 2019, provisional application No. 62/773,197, filed on Nov. 30, 2018.

(51) Int. Cl.
 *H01R 13/52* (2006.01)
 *A61B 5/00* (2006.01)
 *H01R 4/02* (2006.01)
 *A61B 5/1455* (2006.01)

(52) U.S. Cl.
 CPC ..... *H01R 13/5224* (2013.01); *A61B 5/14552* (2013.01); *A61B 5/6847* (2013.01); *H01R 4/023* (2013.01); *A61B 2562/227* (2013.01); *H01R 2201/12* (2013.01)

(58) Field of Classification Search
 CPC ............. H01R 13/5224; H01R 4/023; H01R 2201/12; A61B 5/14552
 USPC ........................................................ 439/357
 See application file for complete search history.

(56) References Cited

U.S. PATENT DOCUMENTS

| | | | |
|---|---|---|---|
| 7,553,191 B2 * | 6/2009 | Su | H01R 13/6658 439/497 |
| 7,555,327 B2 * | 6/2009 | Matlock | A61B 5/6826 600/344 |
| 8,527,038 B2 | 9/2013 | Moon et al. | |
| 9,439,574 B2 | 9/2016 | McCombie et al. | |

(Continued)

FOREIGN PATENT DOCUMENTS

| | | |
|---|---|---|
| CN | 1407668 A | 4/2003 |
| CN | 2728009 Y | 9/2005 |

(Continued)

*Primary Examiner* — Alexander Gilman
(74) *Attorney, Agent, or Firm* — Ming Chieh Chang

(57) ABSTRACT

A cable includes an electrical connector at one end and a sensor at the other end. The connector includes a terminal module having a plurality of contacts embedded within an insulator wherein each contact has a resilient contacting section exposed upon to an exterior in a first vertical direction, and a soldering section exposed in a second vertical direction to be connected to the corresponding wires of the cable and selectively further to a resistor. The sensor includes a case enclosing an LED (Light Emitting Diode) and a PD (Photo Diode both of which are respectively connected to the corresponding contacts respectively soldered to the corresponding wires.

15 Claims, 39 Drawing Sheets

(56) References Cited

U.S. PATENT DOCUMENTS

| | | | |
|---|---|---|---|
| 9,685,744 | B2 | 6/2017 | Little et al. |
| 9,698,545 | B2 | 7/2017 | Little et al. |
| 9,722,375 | B2 | 8/2017 | Chang et al. |
| 2002/0043883 | A1 | 4/2002 | Shimizu |
| 2006/0223351 | A1 | 10/2006 | Kim |
| 2016/0329667 | A1* | 11/2016 | Tsai ................ H01R 13/52 |
| 2018/0062324 | A1* | 3/2018 | Wu ................ H01R 24/64 |

FOREIGN PATENT DOCUMENTS

| | | |
|---|---|---|
| CN | 201252170 Y | 6/2009 |
| CN | 201773994 U | 3/2011 |
| CN | 103168397 A | 6/2013 |
| CN | 103326157 A | 9/2013 |
| CN | 203574208 U | 4/2014 |
| CN | 203617524 U | 5/2014 |
| CN | 205724126 U | 11/2016 |
| CN | 205790482 U | 12/2016 |
| CN | 106921061 A | 7/2017 |
| CN | 207490156 U | 6/2018 |
| CN | 3392971 A | 10/2018 |
| TW | 392929 | 6/2000 |
| TW | 201714363 | 1/2017 |
| TW | M315420 | 7/2017 |
| WO | WO2017083540 A1 | 5/2017 |
| WO | 2018046896 A | 3/2018 |

\* cited by examiner

CABLE ASSEMBLY

BACKGROUND OF THE DISCLOSURE

1. Field of the Disclosure

The present disclosure relates to a cable assembly, and more particularly to the cable assembly with superior waterproof and low cost.

2. Description of Related Arts

U.S. Pat. Nos. 9,439,574, 9,685,744, 9,698,545 and 9,722,375 disclose the medical device and the associated cables which may be used with the human body as shown in U.S. Pat. No. 8,527,038. Although the medical device is structured to be waterproofed, the conventional coupling cable connector of the cable assembly is constructed with relatively inferior waterproofing function. In addition, the traditional coupling connector requires to use a printed circuit board with a resistor mounted thereon, and the FPC used on the SPO2 (Saturation of Peripheral Oxygen) side, thus increasing the cost An improved low cost cable assembly is desired.

SUMMARY OF THE DISCLOSURE

An object of the invention is to provide a cable assembly with superior waterproofing and low cost.

To achieve the above object, a cable assembly includes a cable with an electrical connector at one end and a sensor at the other end. The connector includes a terminal module having a plurality of contacts embedded within an insulator wherein each contact has a resilient contacting section exposed upon to an exterior in a first vertical direction, and a soldering section exposed in a second vertical direction to be connected to the corresponding wires of the cable and selectively further to a resistor. The sensor includes a case enclosing an LED (Light Emitting Diode) and a PD (Photo Diode both of which are respectively connected to the corresponding contacts respectively soldered to the corresponding wires.

Other objects, advantages and novel features of the disclosure will become more apparent from the following detailed description when taken in conjunction with the accompanying drawings.

BRIEF DESCRIPTION OF THE DRAWINGS

FIG. 18 is a top view of the electrical connector of FIG. 12;

DETAILED DESCRIPTION OF THE PREFERRED EMBODIMENT

Figure 1A:
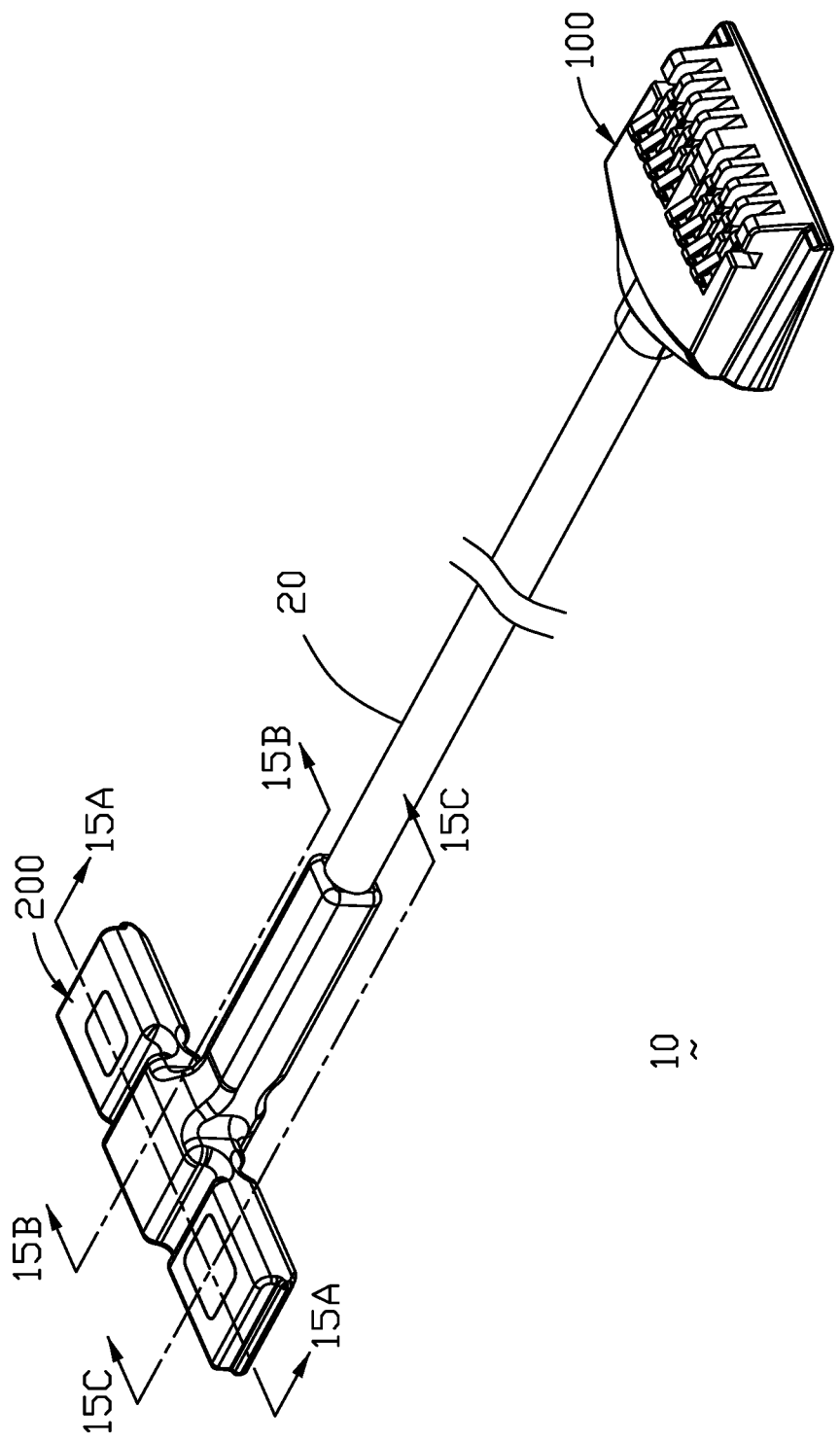
FIG. 1(A) is a perspective view of a cable assembly according to a first embodiment of the invention.
Figure 1B:
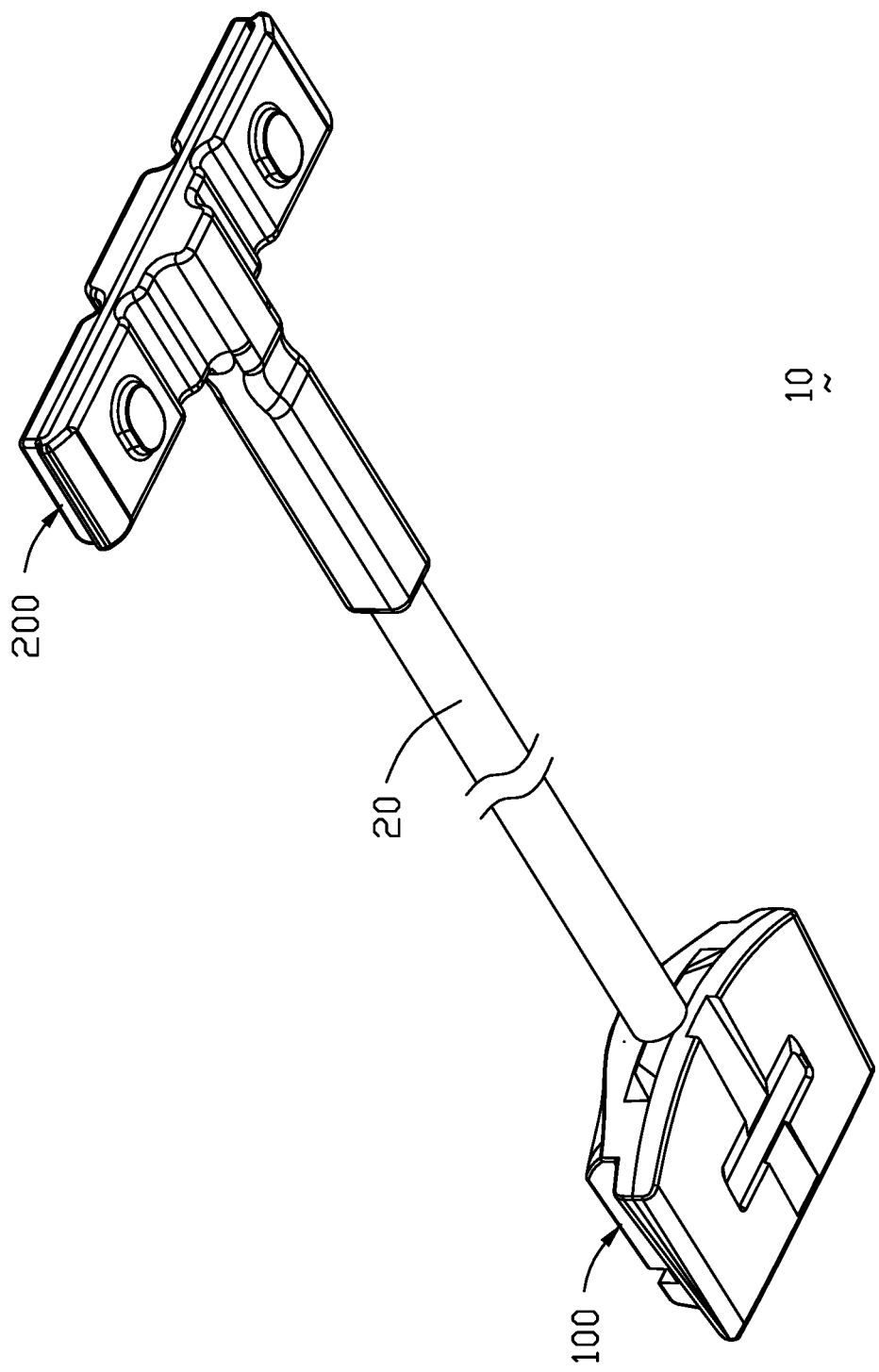
FIG. 1(B) is another perspective view of the cable assembly of FIG. 1(A)
Figure 2A:
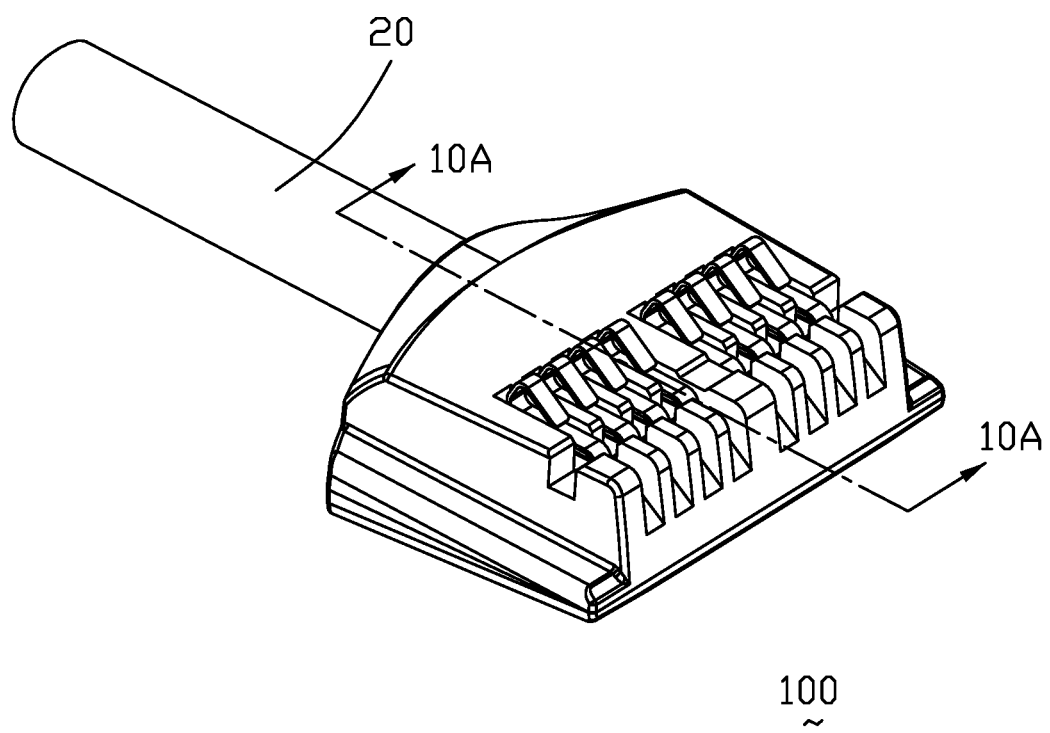
FIG. 2(A) is a perspective view of the connector of the cable assembly of FIG. 1(A)
Figure 2B:
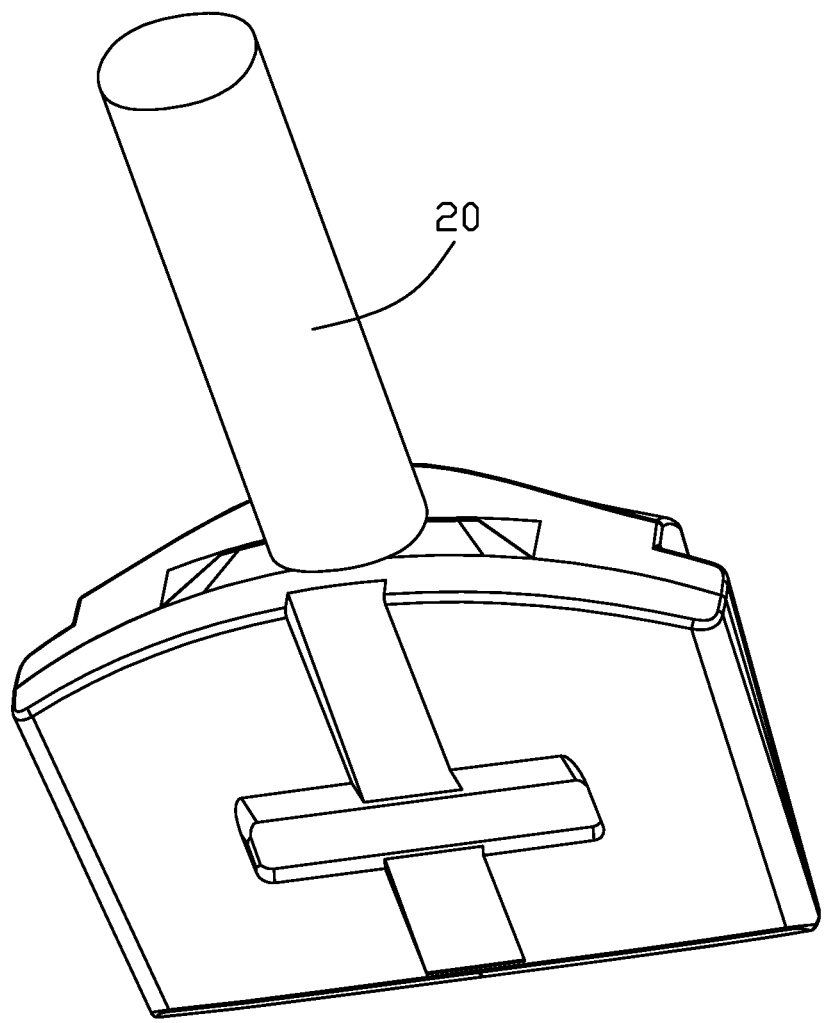
FIG. 2(B) is another perspective view of the electrical connector of the cable assembly of FIG. 2(A)
Figure 3:
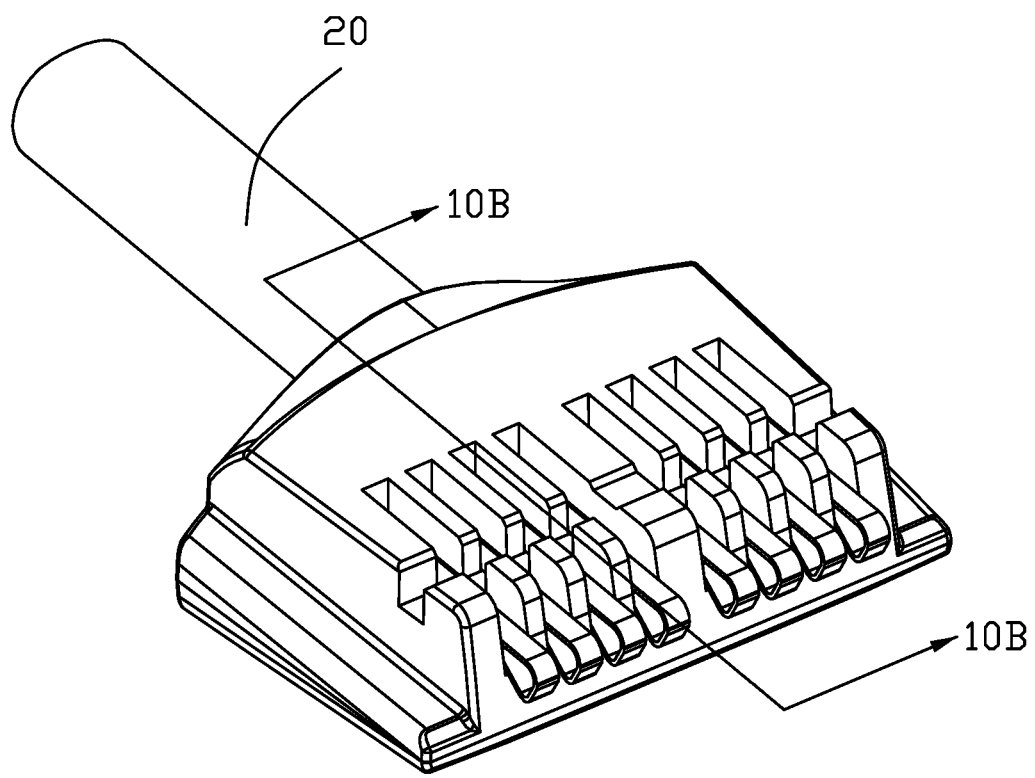
FIG. 3 is a perspective view of the electrical connector of the cable assembly of FIG. 2(A) wherein the contacts have not been bent to their final positions.
Figure 4A:
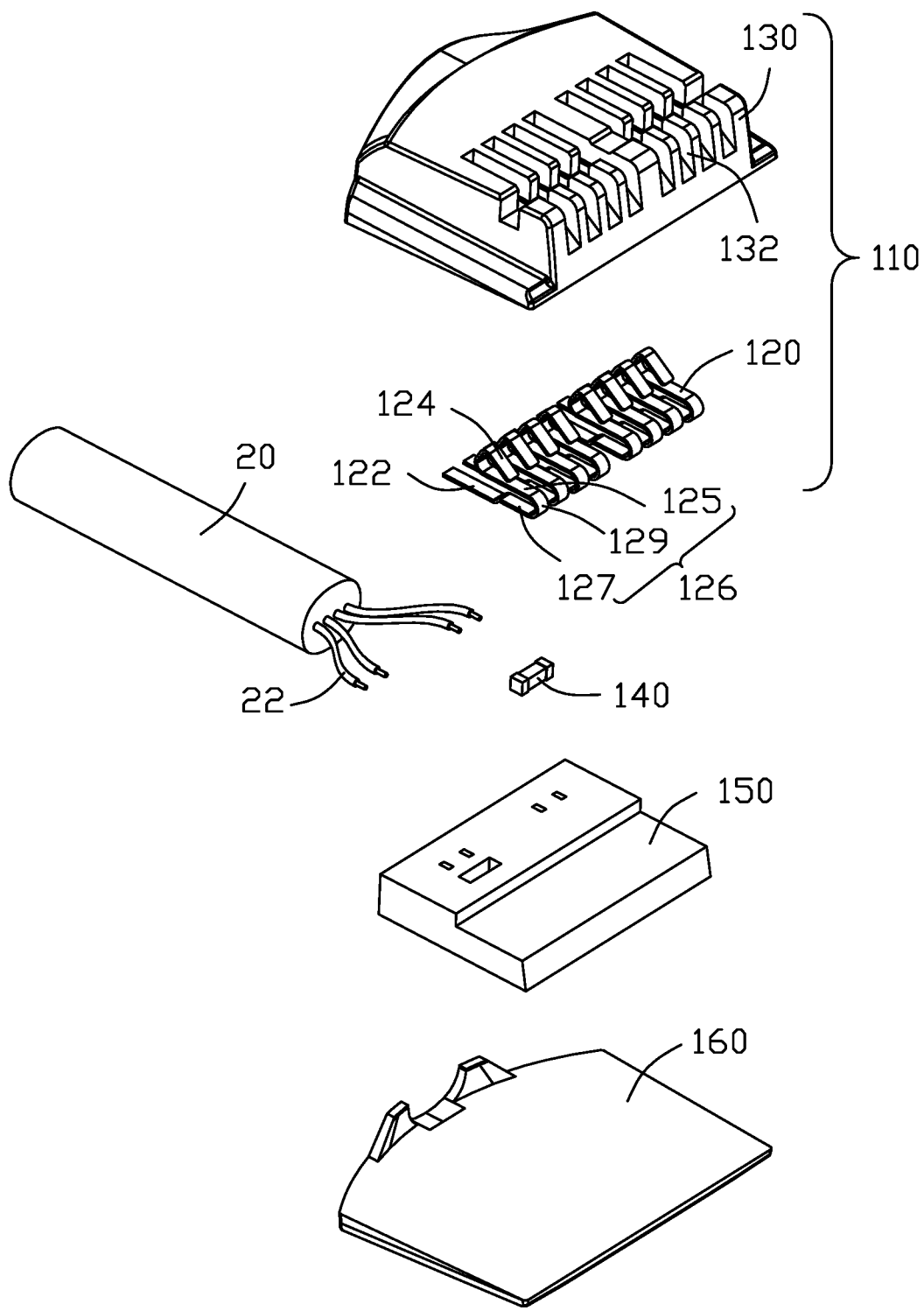
FIG. 4(A) is an exploded perspective view of the electrical connector of the cable assembly of FIG. 2(A)
Figure 4B:
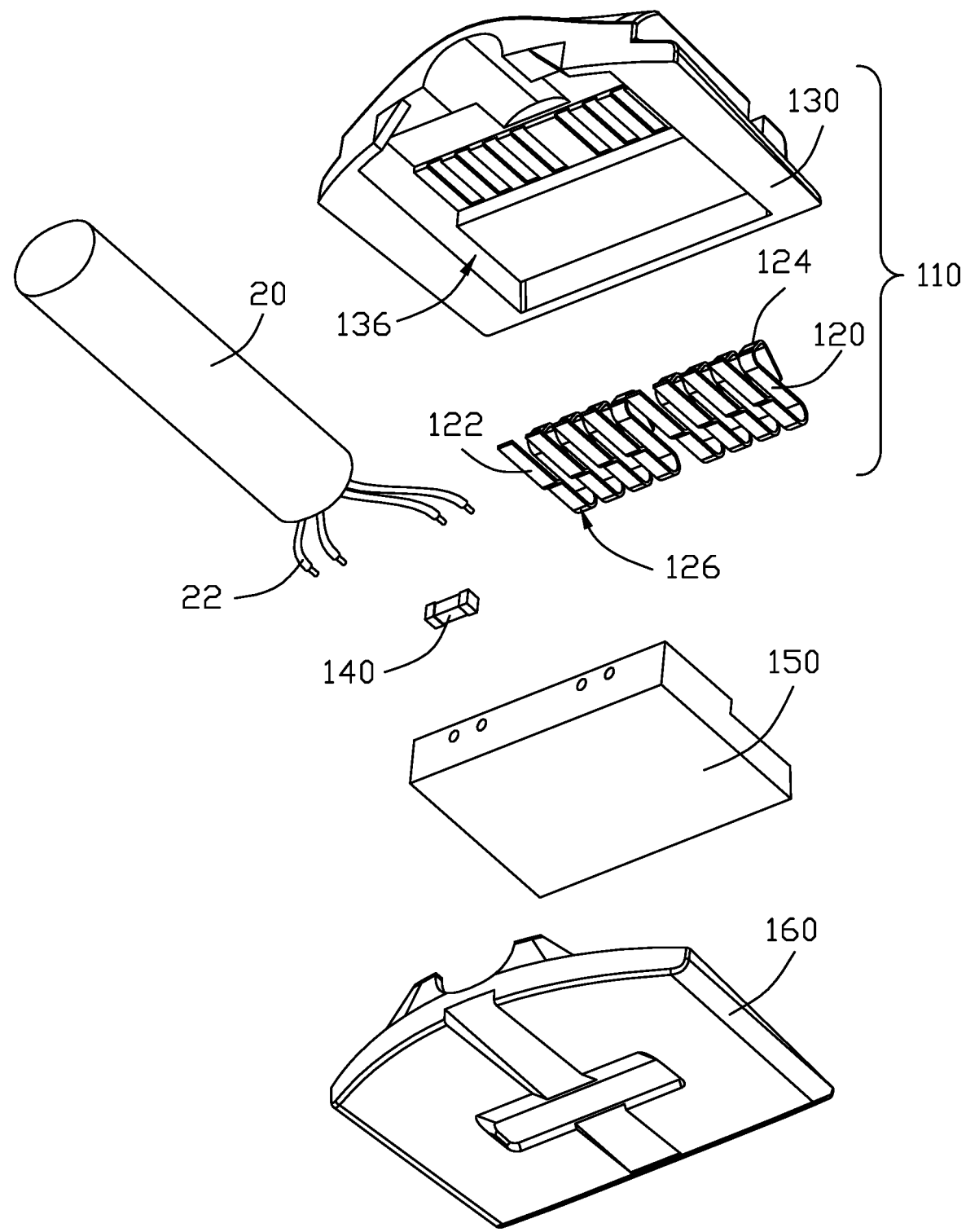
FIG. 4(B) is another exploded perspective view of the electrical connector of the cable assembly of FIG. 4(A)
Figure 5:
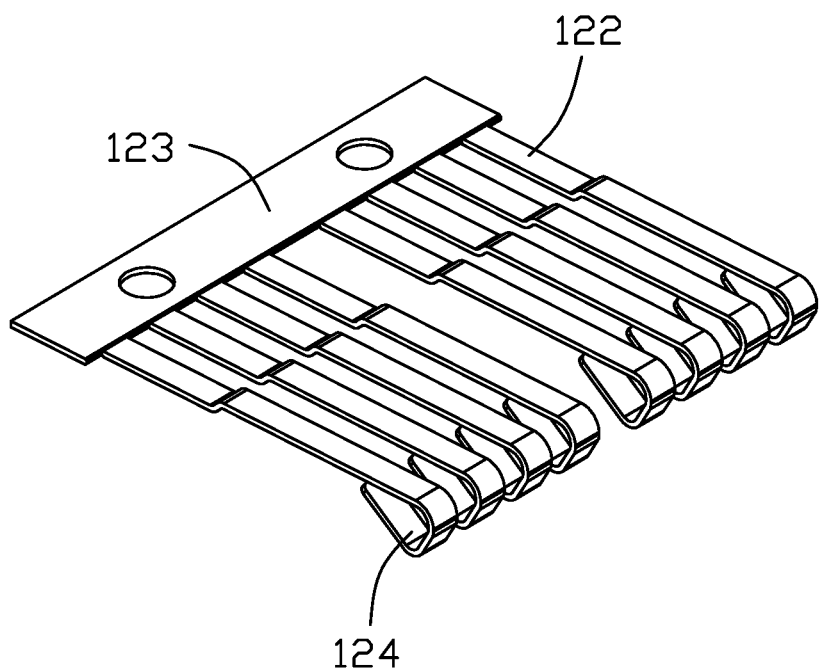
FIG. 5 is a plurality of contacts linked on a contact carrier of the electrical connector of the cable assembly of FIG. 3 wherein the contacts have not been bent to their final positions.
Figure 6:
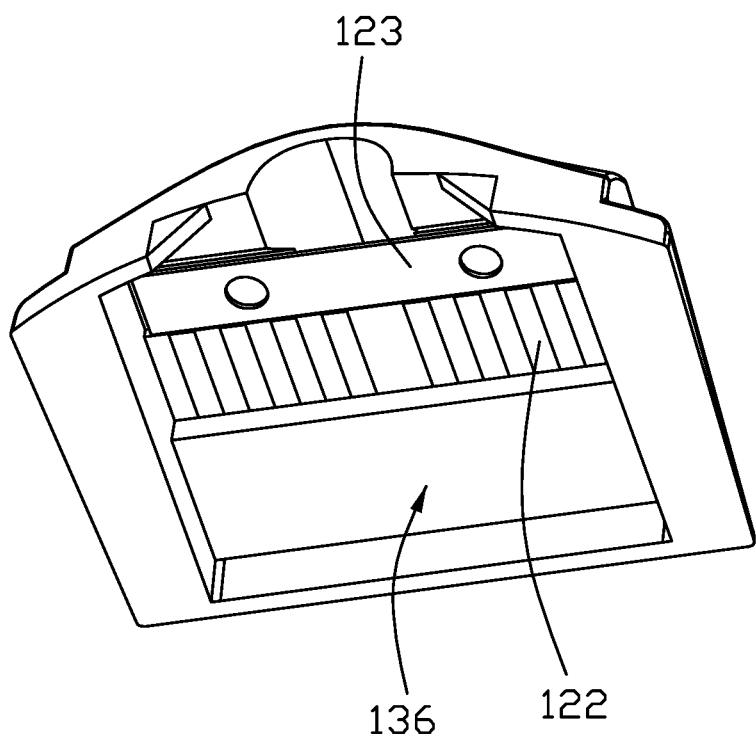
FIG. 6 is a perspective view of a partially assembled electrical connector of the cable assembly of FIG. 2(A)
Figure 7:
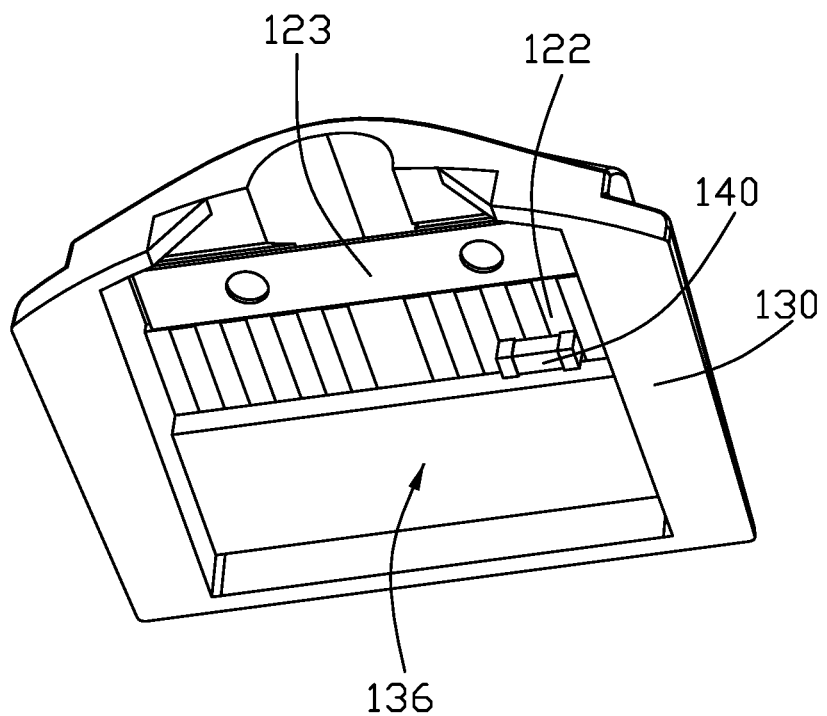
FIG. 7 is a perspective view of a further partially assembled electrical connector of the cable assembly of FIG. 6.
Figure 8:
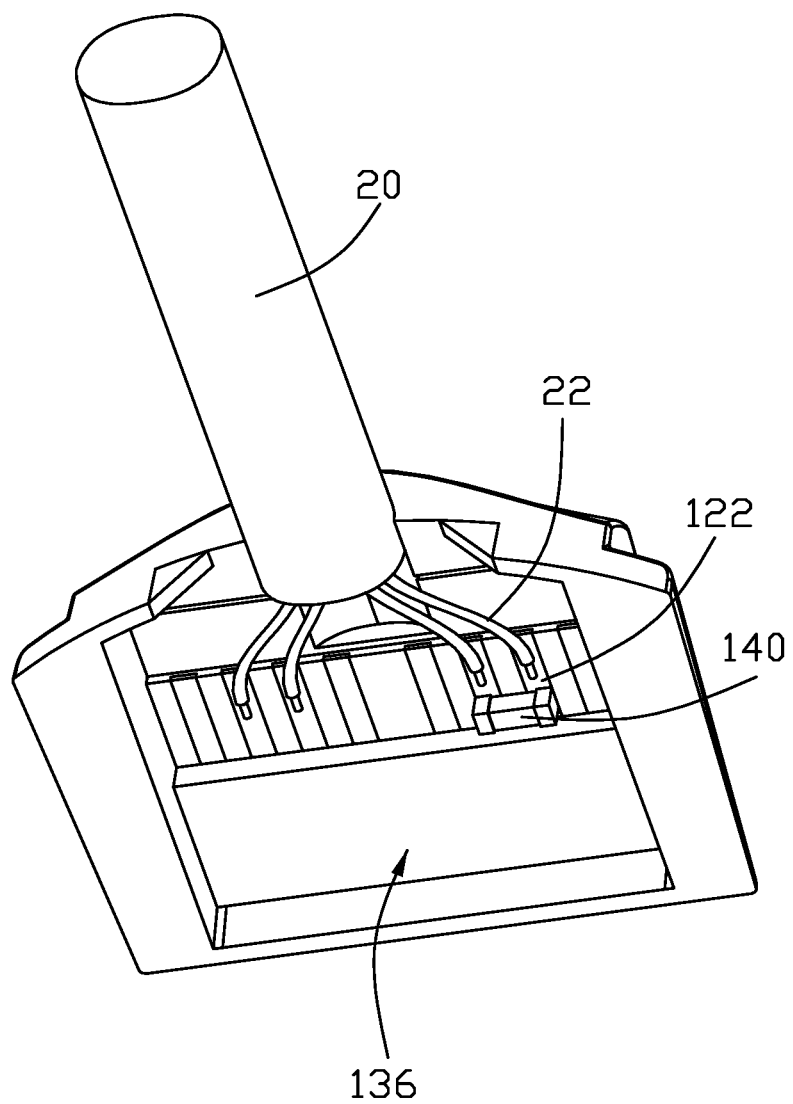
FIG. 8 is a perspective view of a further partially assembled electrical connector of the cable assembly of FIG. 7.
Figure 9:
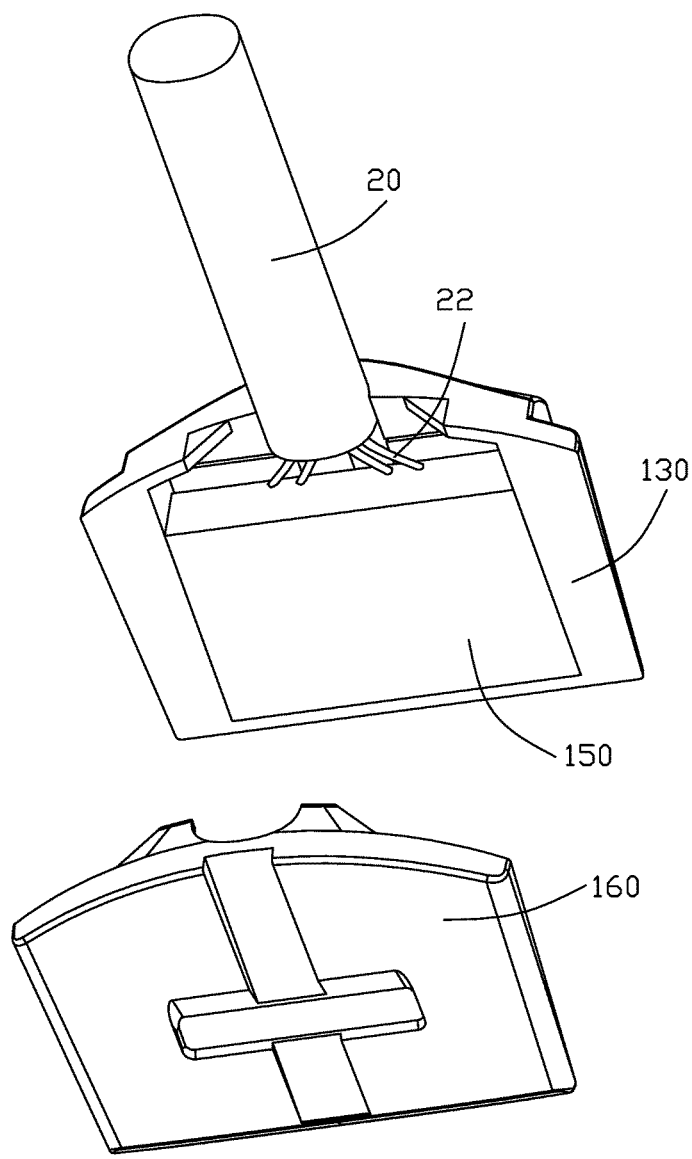
FIG. 9 is an exploded perspective view of the electrical connector of the cable assembly of FIG. 2(A)

Reference numerals are used to describe in detail to only the referred embodiment of the present disclosure.

Figure 10A:
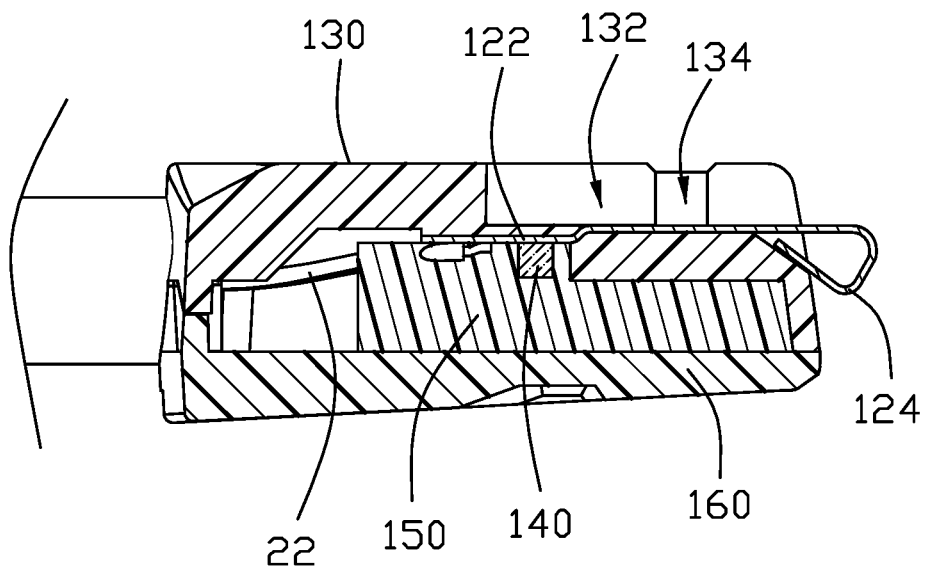
FIG. 10(A) is a cross-sectional view of the electrical connector of the cable assembly of FIG. 3.
Figure 10B:
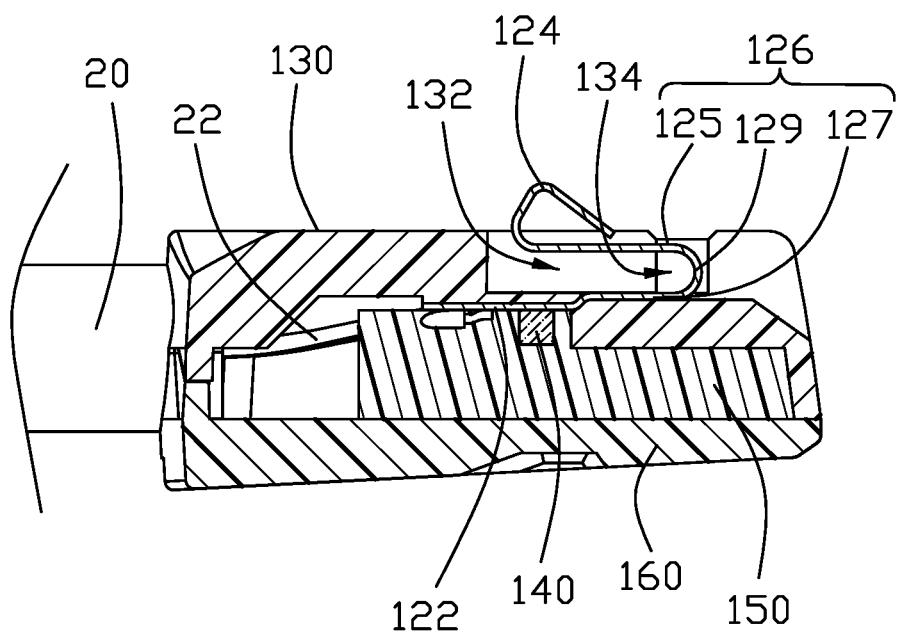
FIG. 10(B) is a cross-sectional view of the electrical connector of the cable assembly of FIG. 2(A)
Figure 10C:
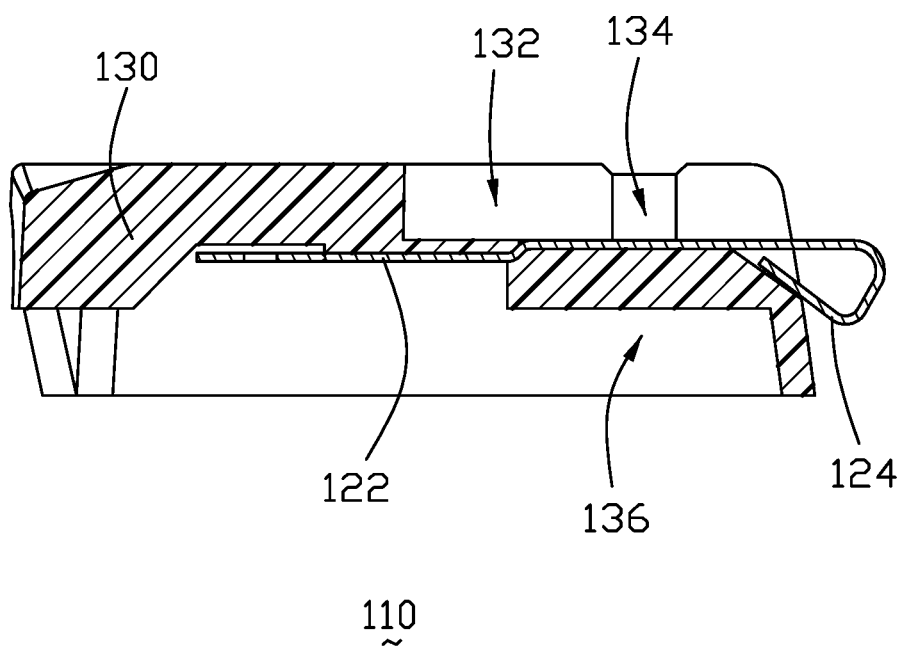
FIG. 10(C) is a cross-sectional view of a partially assembled electrical connector of FIG. 3.
Figure 11:
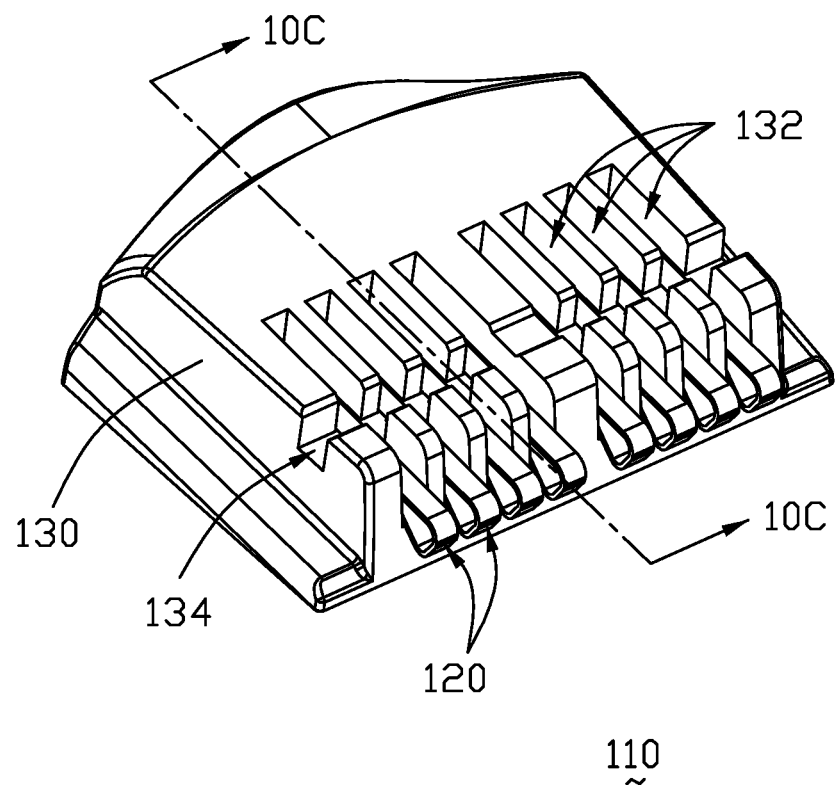
FIG. 11 is a perspective view of the partially assembled electrical connector of FIG. 10(C)
Figure 12A:
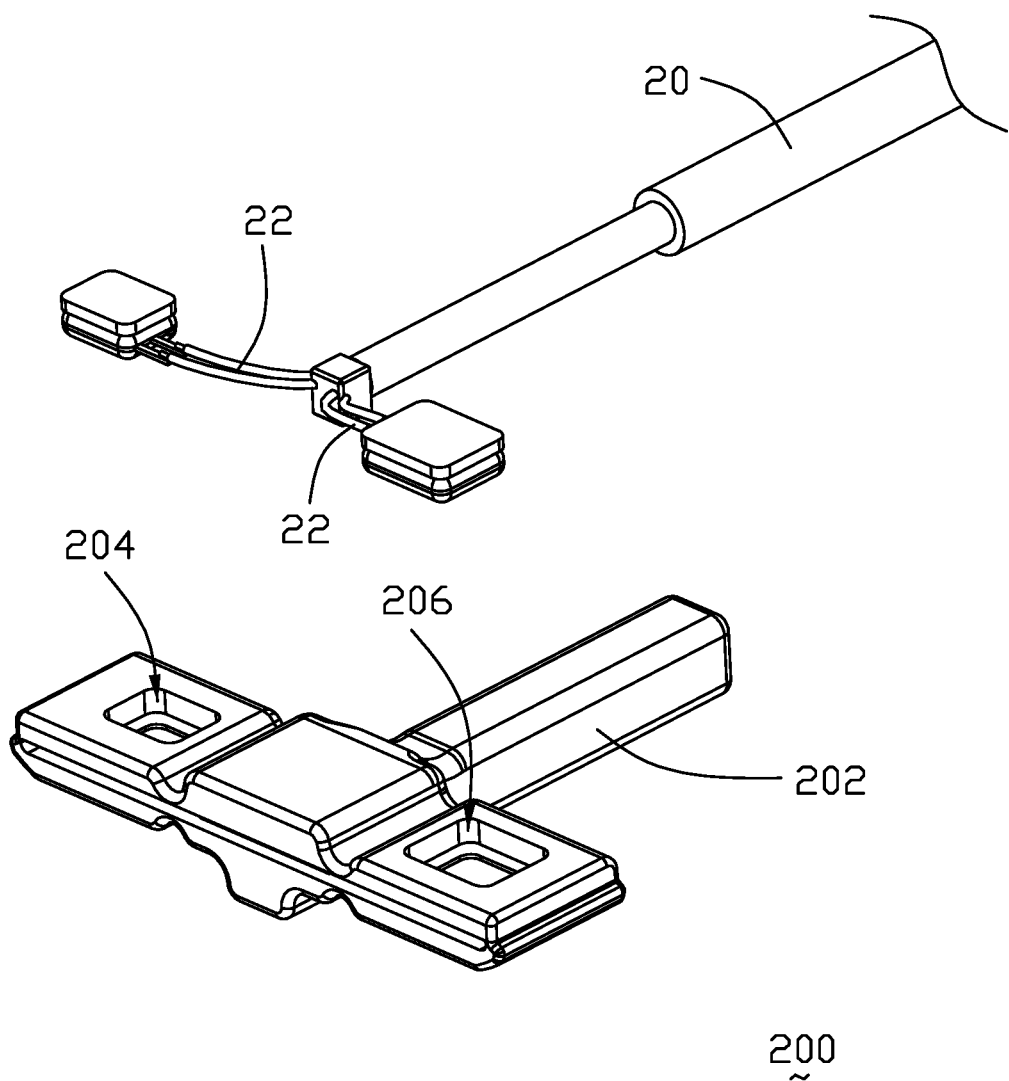
FIG. 12(A) is a perspective view of the sensor sub-assembly of the cable assembly of FIG. 1(A)
Figure 12B:
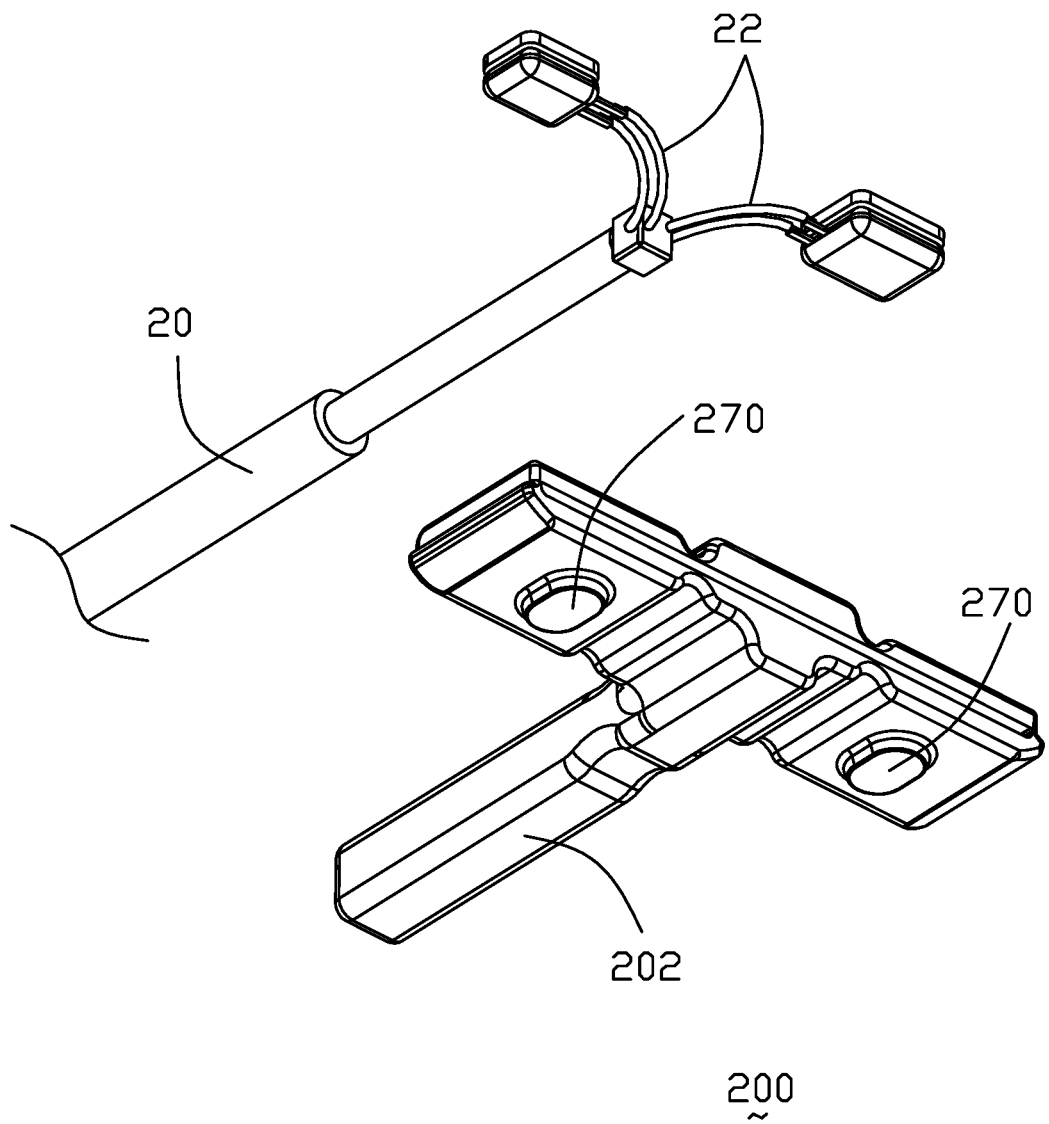
FIG. 12(B) is another perspective view of the sensor sub-assembly of the cable assembly of FIG. 1(A)
Figure 13A:
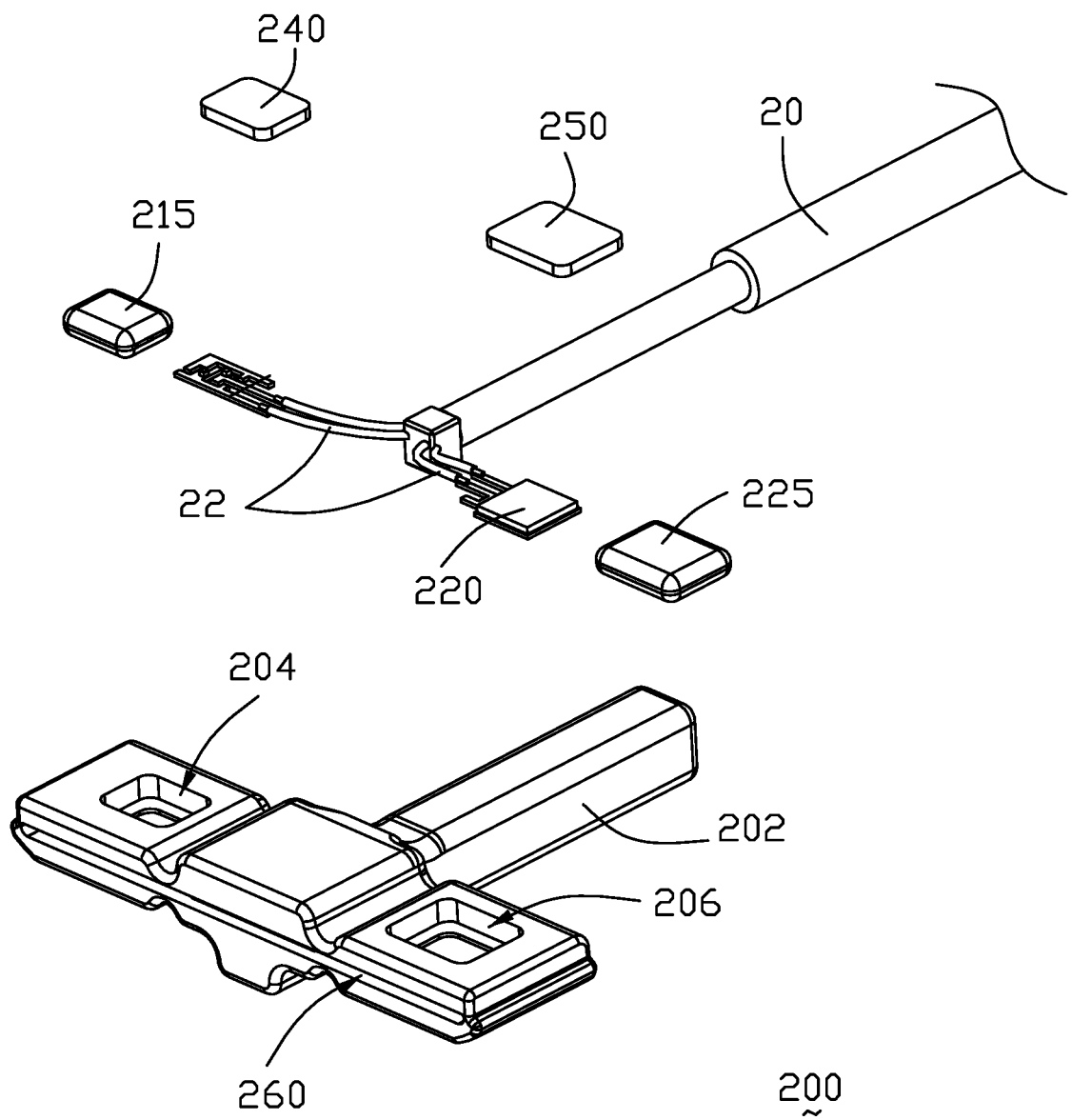
FIG. 13(A) is an exploded perspective view of the sensor sub-assembly of the cable assembly of FIG. 12(A)
Figure 13B:
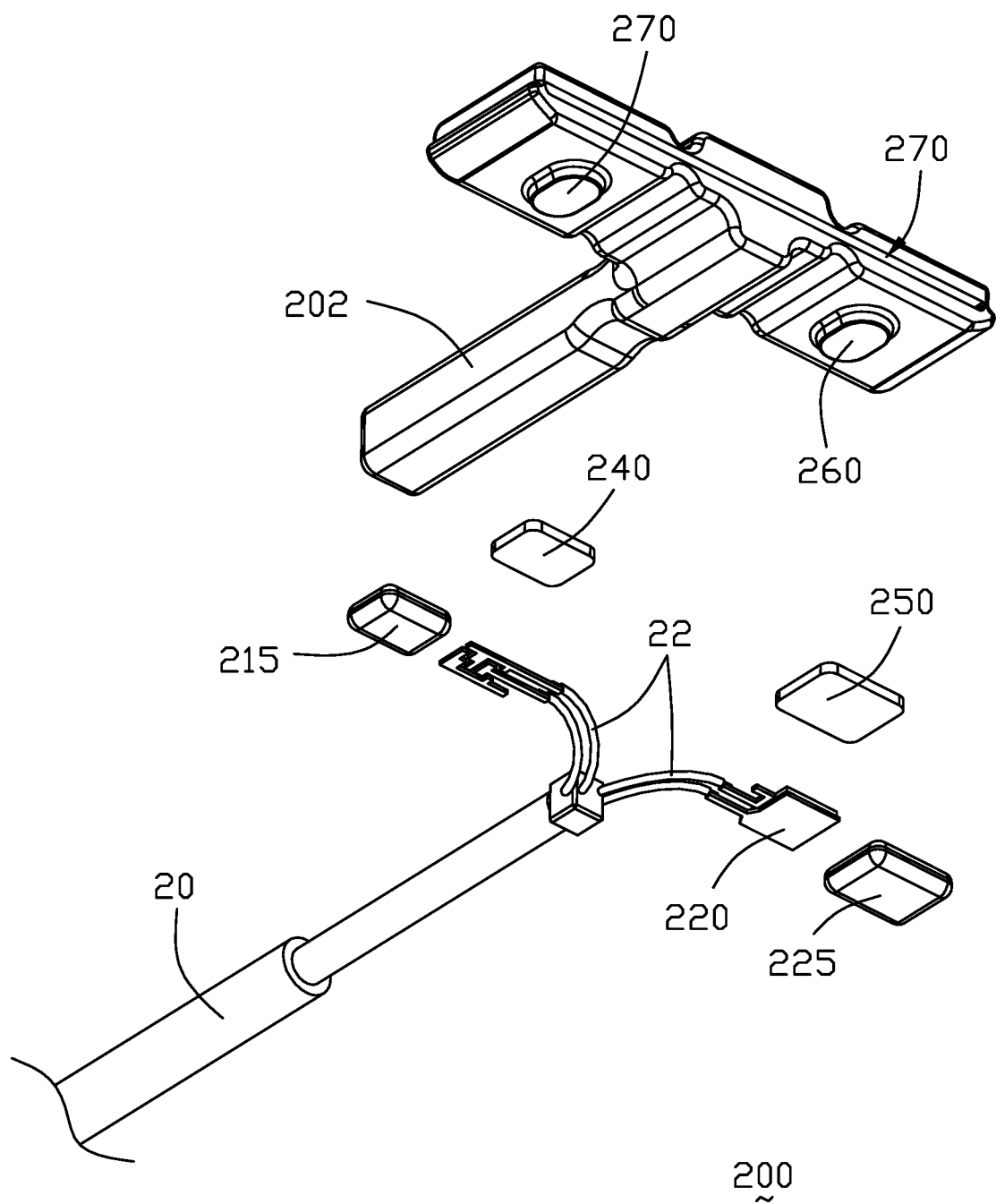
FIG. 13(B) is another exploded perspective view of the sensor sub-assembly of the cable assembly of FIG. 13(A)
Figure 14A:
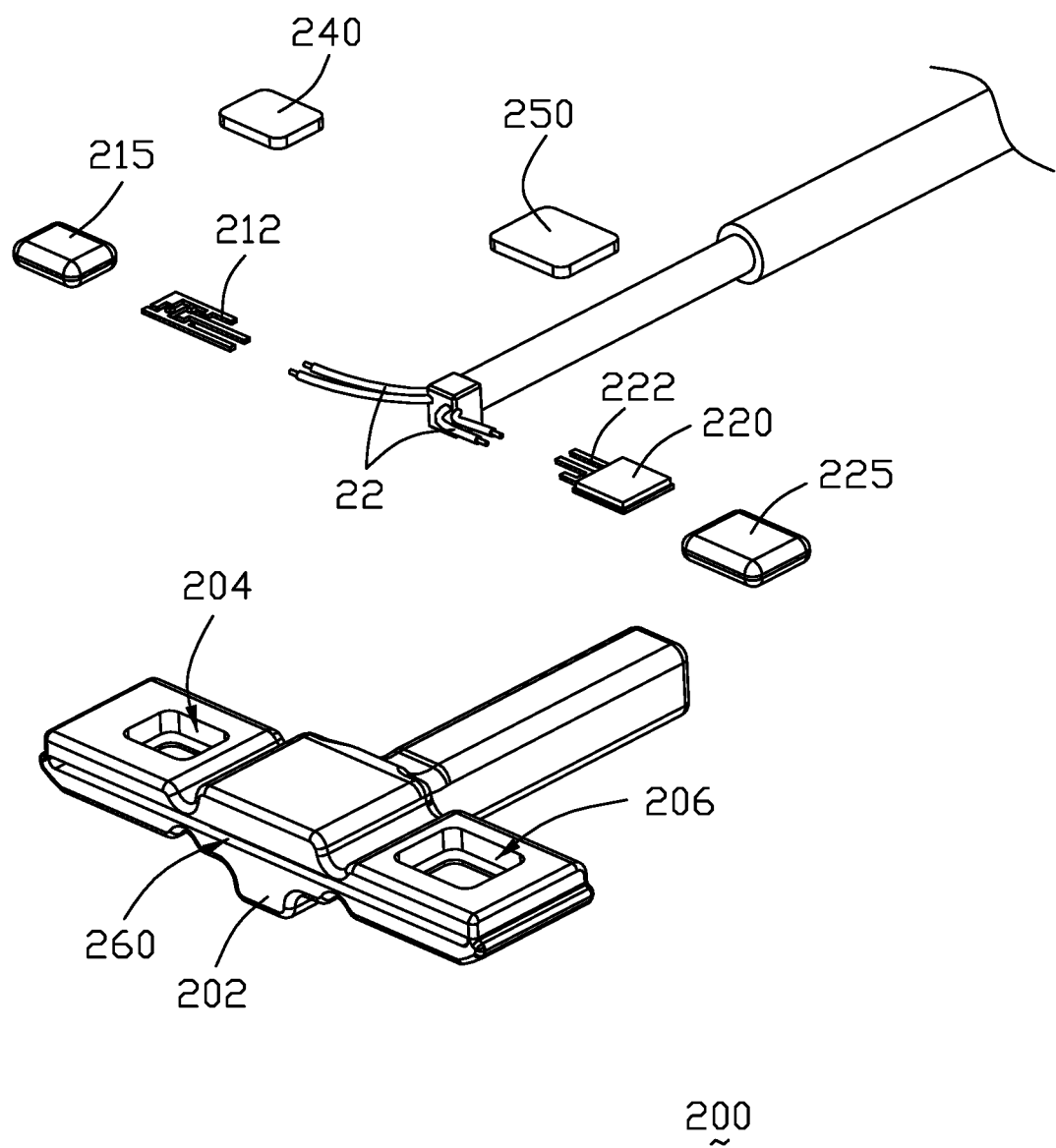
FIG. 14(A) is a further exploded perspective view of the sensor sub-assembly of the cable assembly of FIG. 13(A)
Figure 14B:
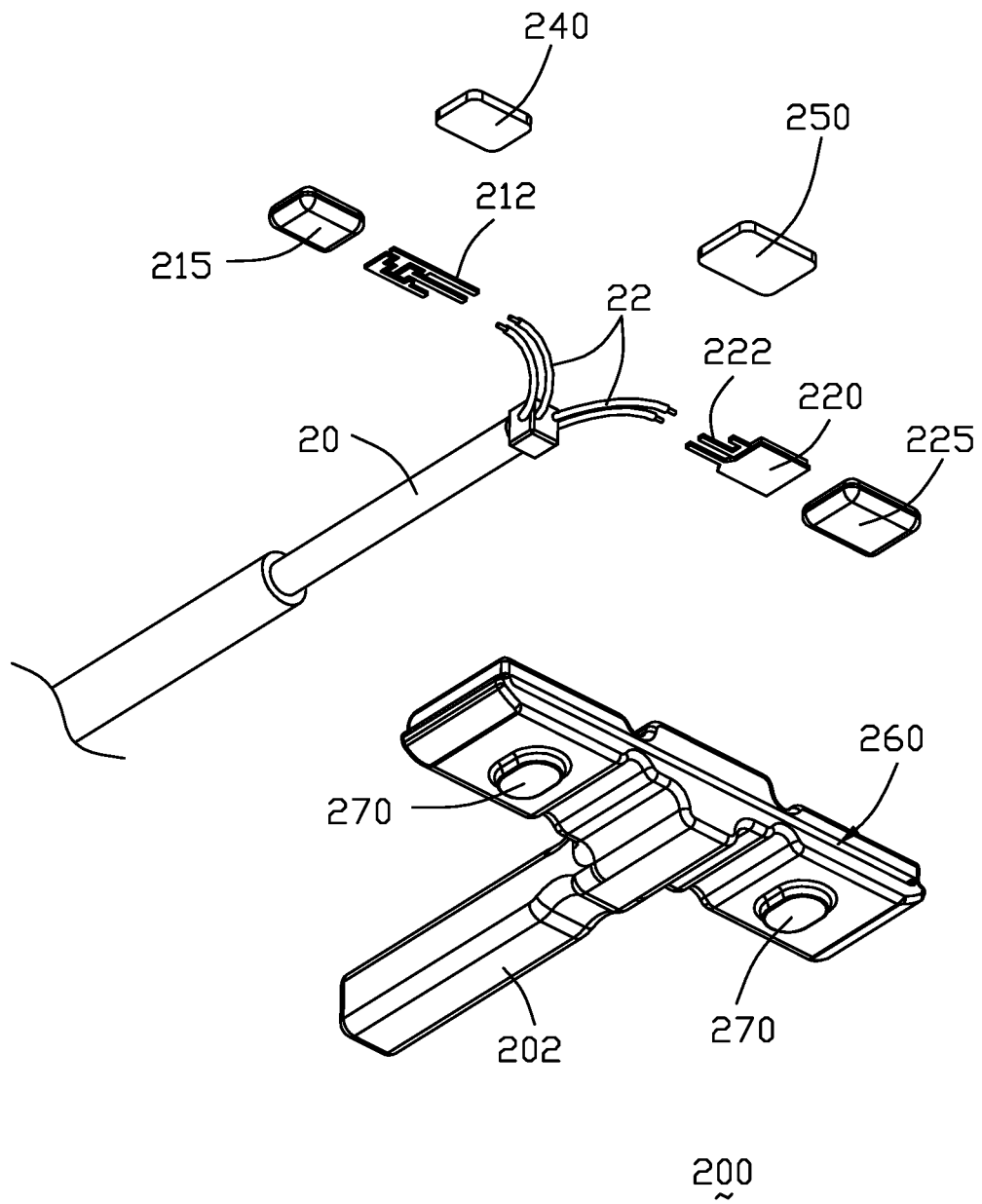
FIG. 14(B) is another further exploded perspective view of the sensor sub-assembly of the cable assembly of FIG. 14(A)
Figure 15A:
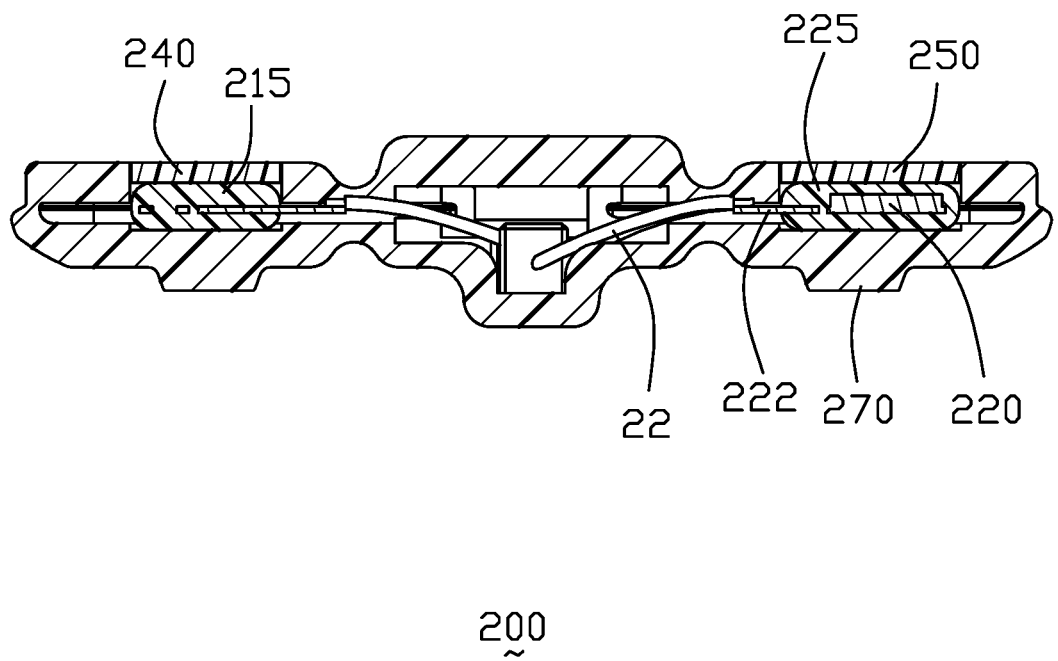
FIG. 15(A) is a cross-sectional view of the sensor sub-assembly of the cable assembly of FIG. 1(A)
Figure 15B:
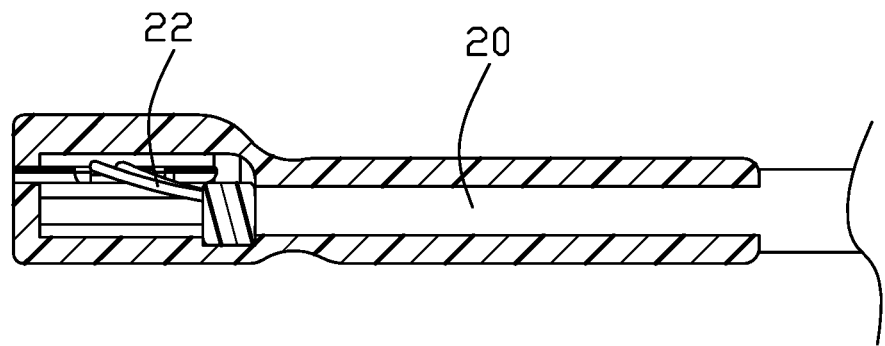
FIG. 15(B) is a cross-sectional view of the sensor sub-assembly of the cable assembly of FIG. 1(A)
Figure 15C:
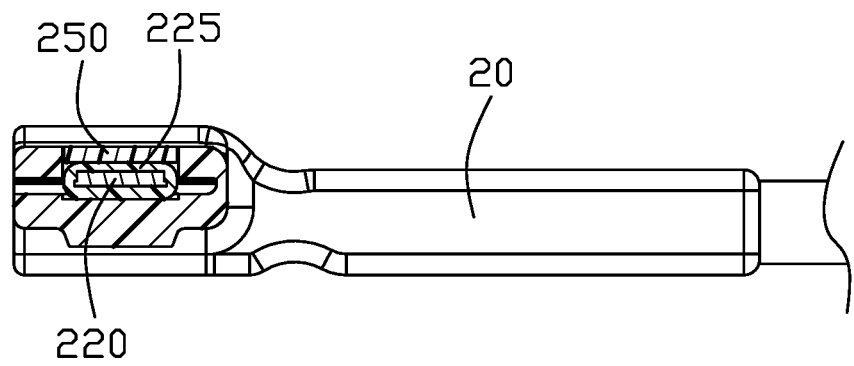
FIG. 15(C) is a cross-sectional view of the sensor sub-assembly of the cable assembly of FIG. 1(A)
Figure 16A:
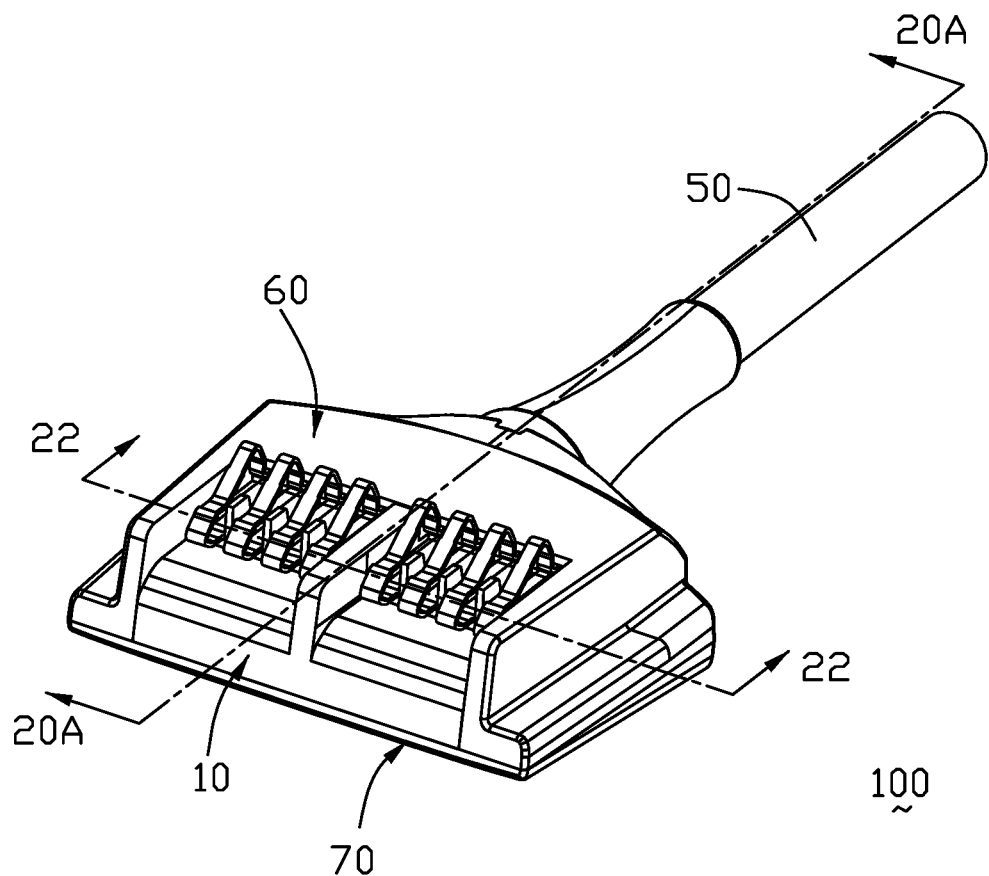
FIG. 16(A) is a perspective view of the cable connector assembly according to a second embodiment of the invention.
Figure 16B:
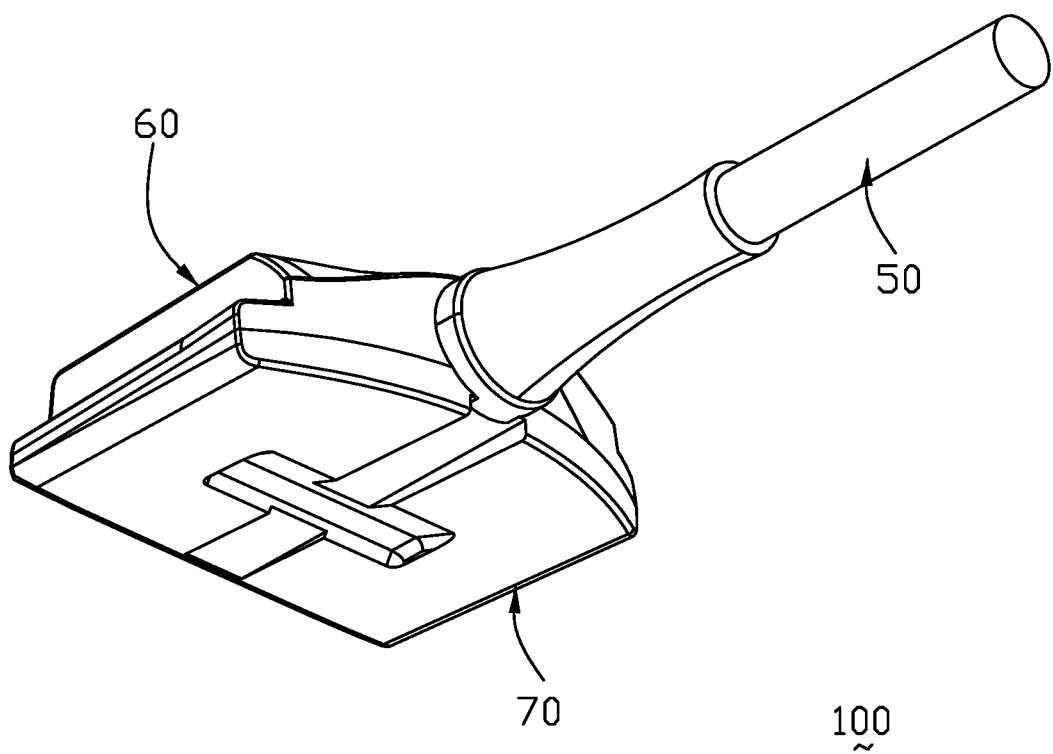
FIG. 16(B) is another perspective view of the cable connector assembly of FIG. 16(A)
Figure 17A:
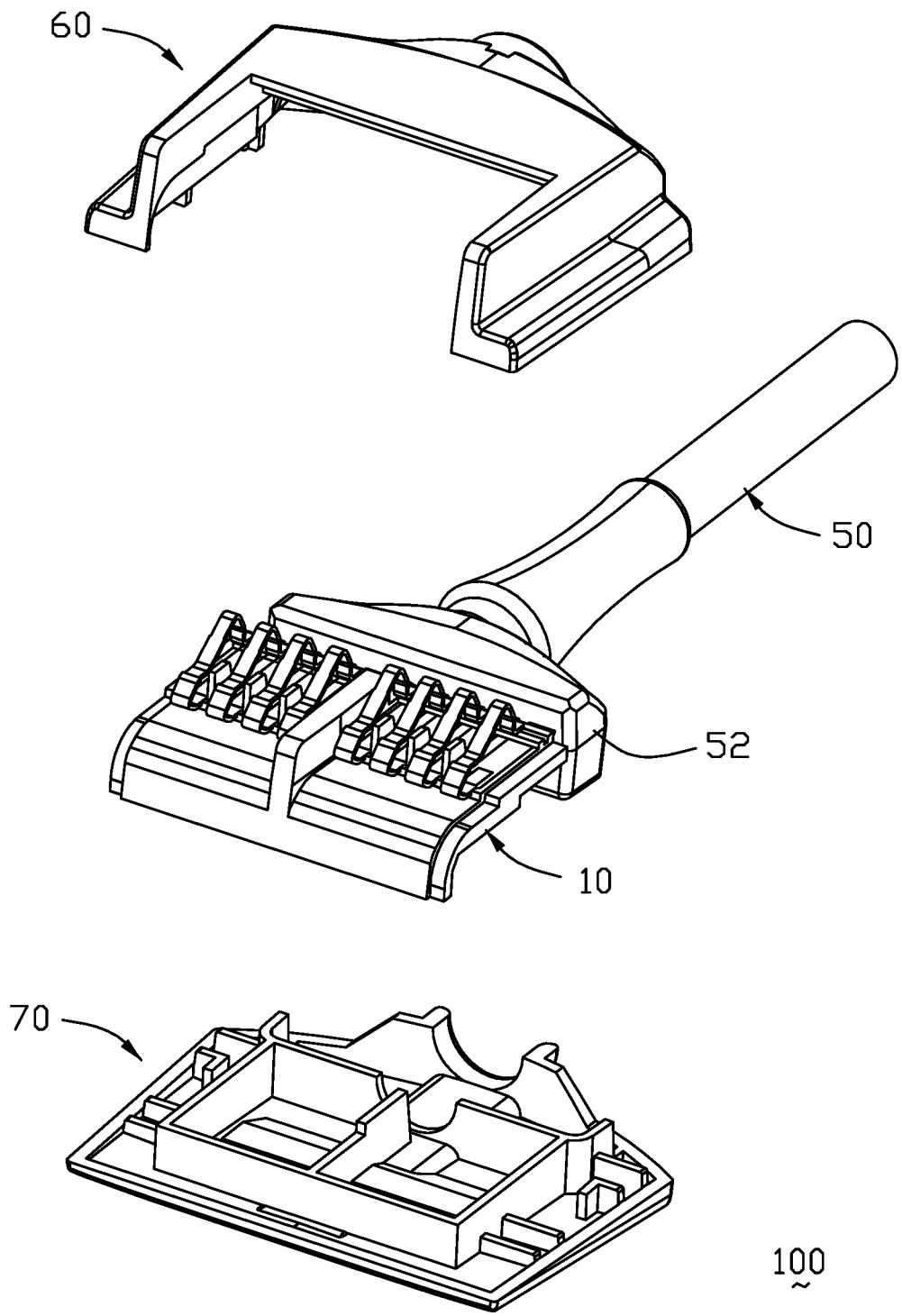
FIG. 17(A) is an exploded perspective view of the cable connector assembly of FIG. 16(A)
Figure 17B:
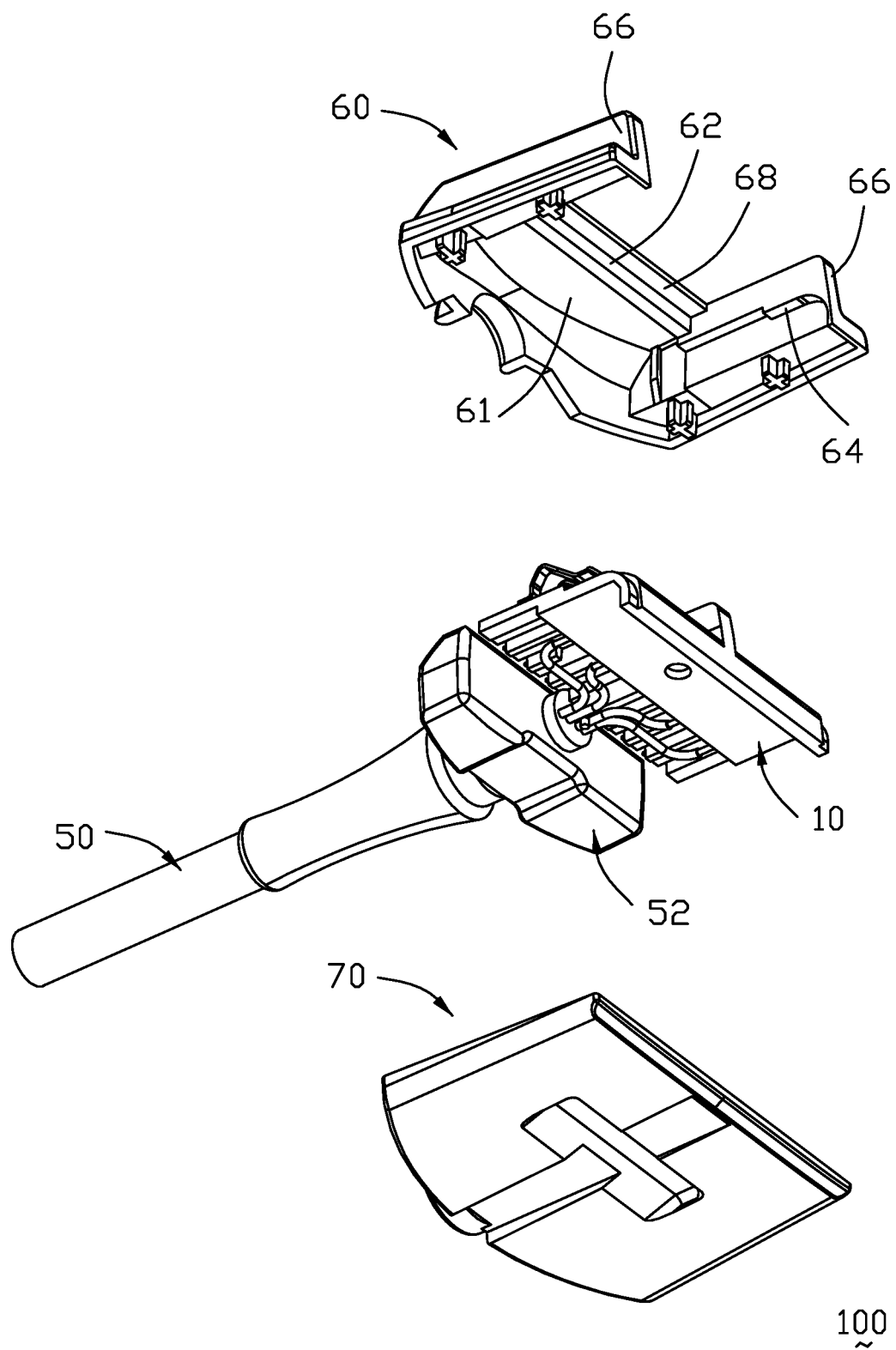
FIG. 17(B) is another exploded perspective view of the cable connector assembly of FIG. 17(A)
Figure 18A:
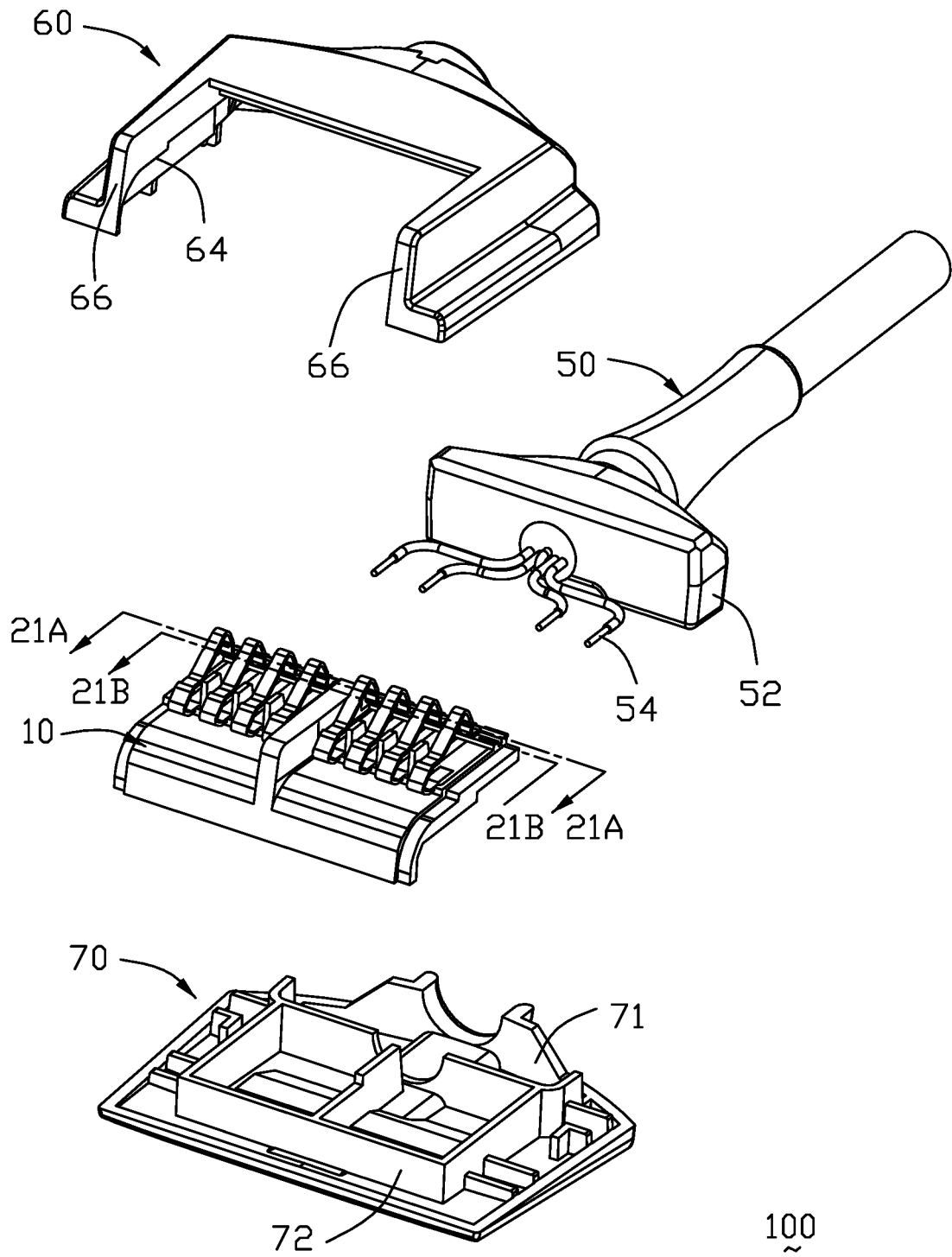
FIG. 18(A) is a further exploded view of the cable connector assembly of FIG. 17(A)
Figure 18B:
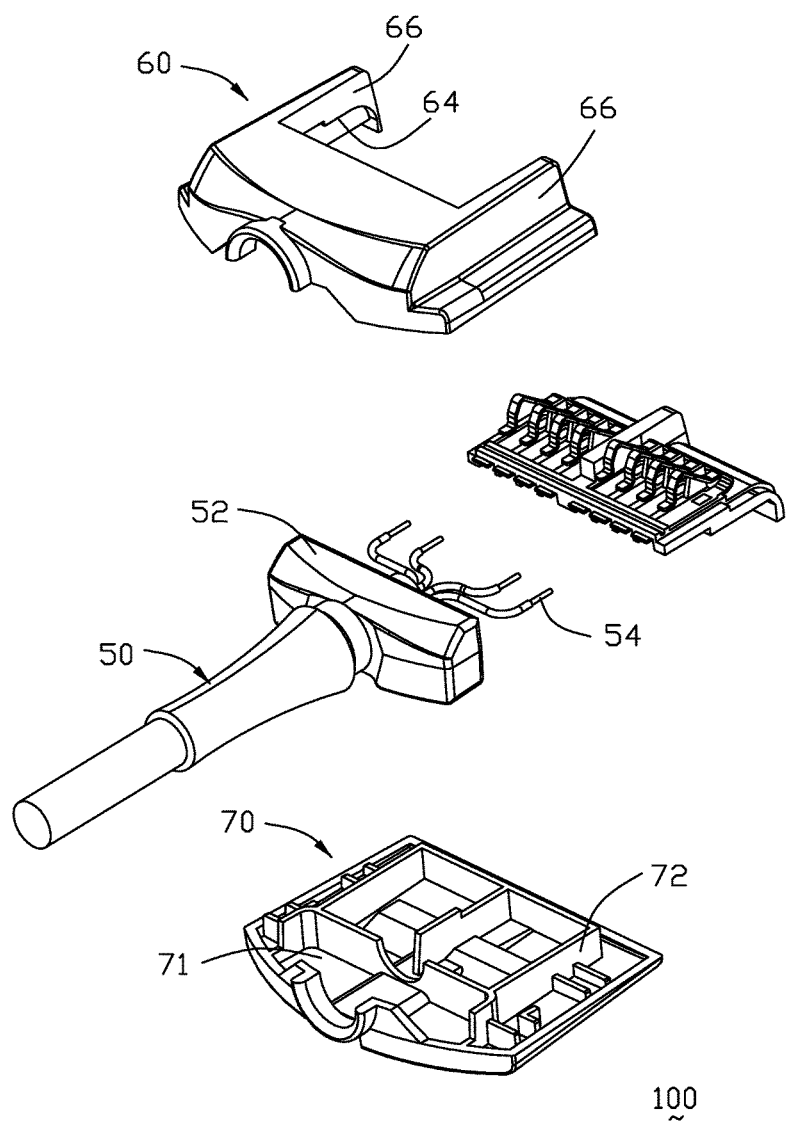
FIG. 18(B) is another exploded perspective view of the cable connector assembly of FIG. 18(A)
Figure 18C:
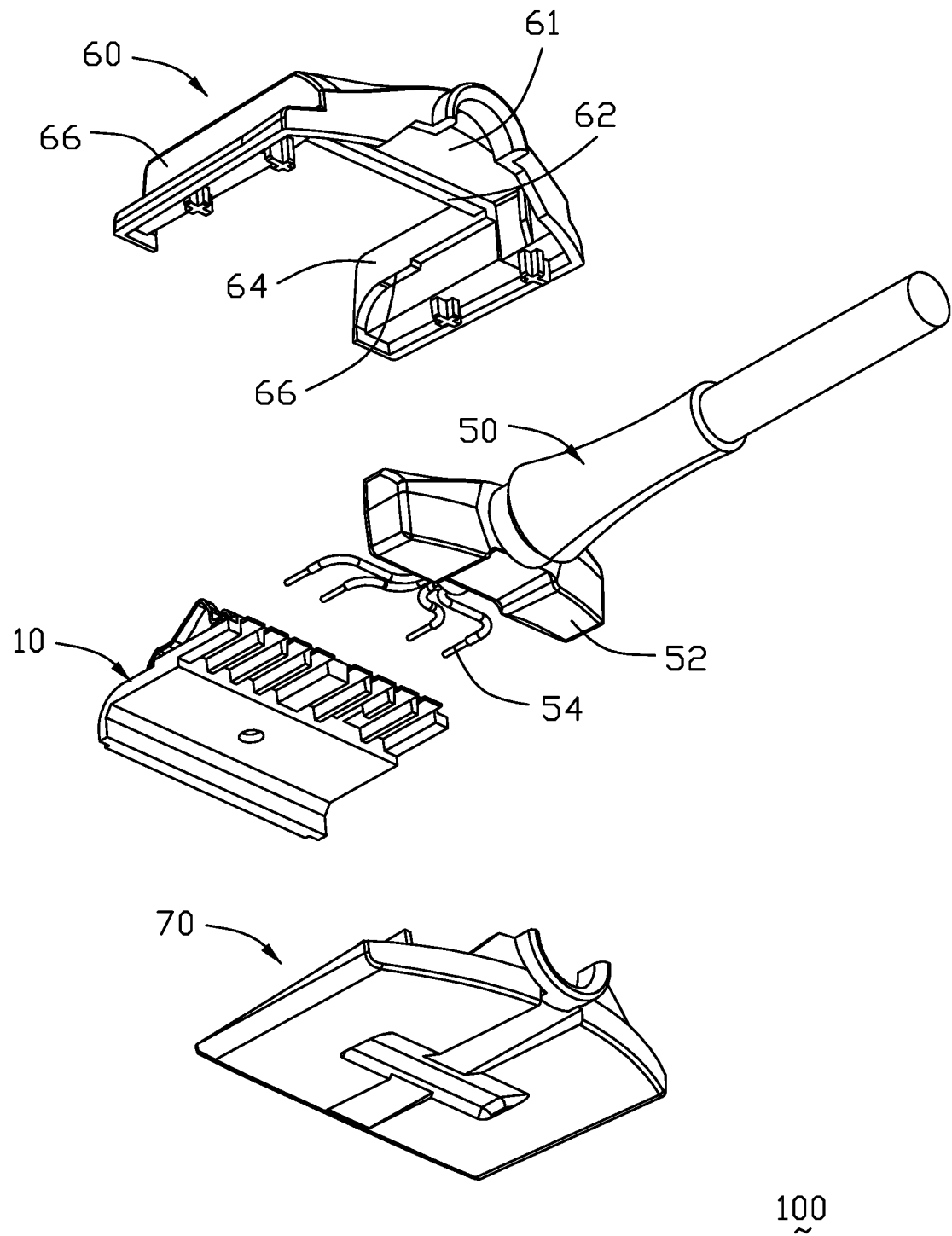
FIG. 18(C) is another exploded perspective view of the cable connector assembly of FIG. 18(A)
Figure 19A:
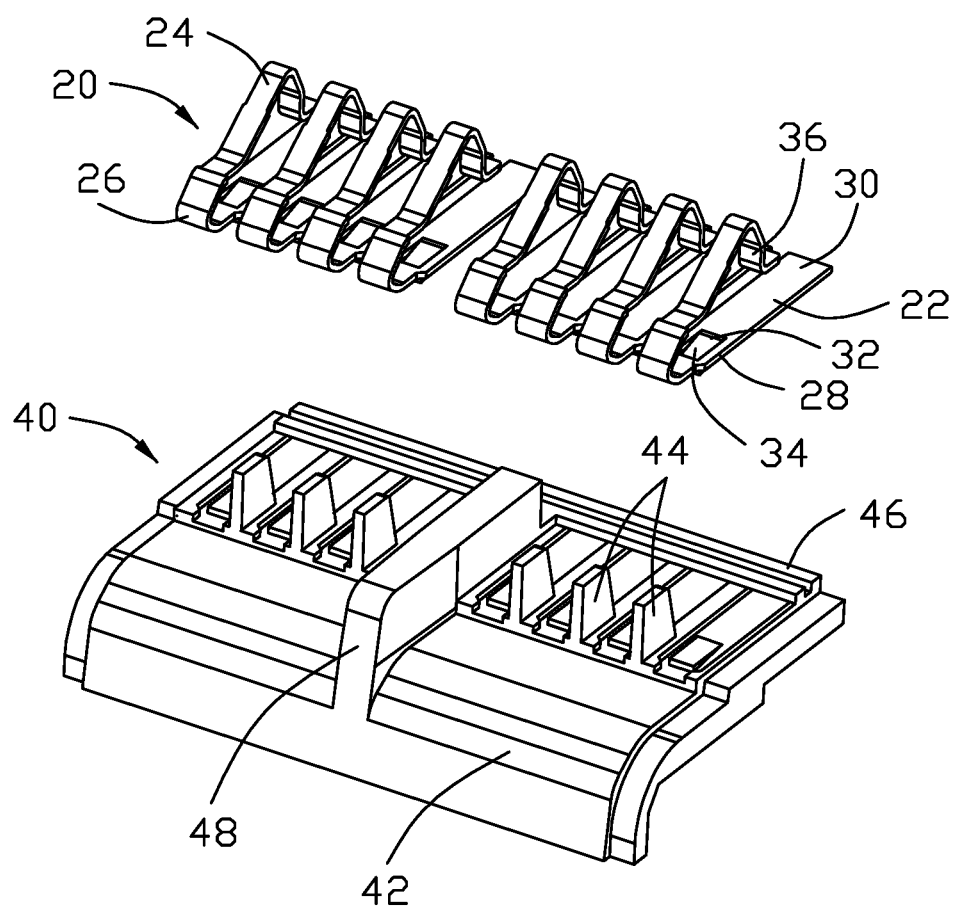
FIG. 19(A) is an exploded view of the contact module of the cable connector assembly of FIG. 18(A)
Figure 19B:
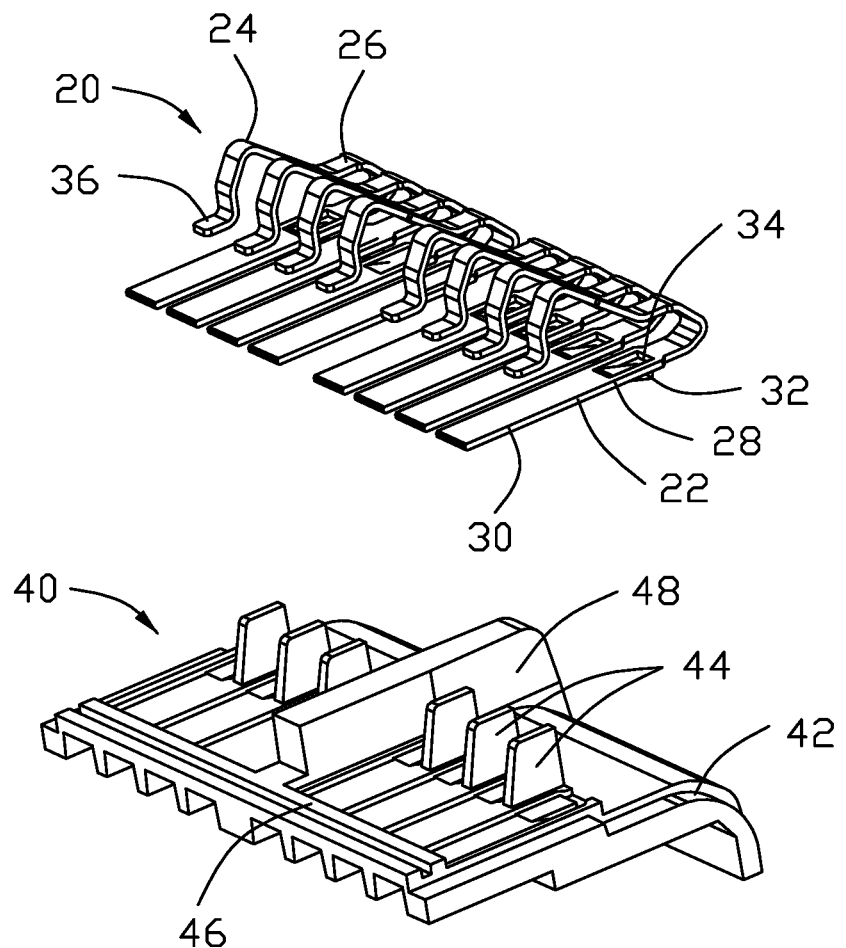
FIG. 19(B) is another exploded perspective view of the cable connector assembly of FIG. 19(A)

A cable assembly 10 includes a cable 20 with an electrical connector 100 at one end and a sensor sub-assembly 200 at the other end. The connector 100 includes a terminal module 110 having a plurality of contacts 120 integrally formed within an insulative housing 130 via an insert-molding process. The housing 130 forms a plurality of passageways 132 exposed to an exterior both vertically and forwardly. A transverse groove 134 extends across the passageways 132 and is exposed upon an upper surface of the housing 130. Each contact 120 includes a rear soldering section 122 exposed downwardly, an upper contacting section 124 exposed upwardly above the corresponding passageway 132, a U-shaped middle section 126 between the upper contacting section 124 and the rear soldering section 122 and within the corresponding passageway 132. The U-shaped middle section 126 includes an upper arm 125 linked to the contacting section 124, a lower arm 127 supportably seated upon the housing 130, and a bight 129 between the upper arm 125 and the lower arm 127 and within the transverse groove 134. Notably, the contact 120 initially extends along the front-to-back direction as shown in FIG. 10(A), and successively is backwardly bent to form the bight 129 via assistance of a pressing bar (not shown) which is inserted into the transverse groove 134 to downward press the contacts 120 as a fulcrum for folding the contacts 120 so as to have the contacting section 124 exposed upon the upper face of the housing 130 while being downwardly deflectable to enter the corresponding passageway 132 when the contacting section 124 is downwardly pressed by a complementary connector in the cradle part as disclosed in the aforementioned patents. Understandably. The pressing bar will be removed backwardly in the transverse direction after the U-shaped middle section 126 is formed with the final shape.

The wires 22 of the cable 20 are electrically and mechanically connected to the soldering sections 122 of the corresponding contacts 120, respectively. At least one resistor 140 is connected between soldering sections 122 of the two selected neighboring contacts 120 for regulating the corresponding power. A glue block 150 is applied upon the underside of the housing 130 to protectively cover the soldering section 122, the wires 22 and the resistor 140. Notably, because the housing 120 forms a cavity 136 in the underside, the glue block 150 can flow into and further be retained in the cavity 136 and solidified. Finally, a cap 160 is attached upon the underside of the housing 130 to cover the cavity 136.

One feature of the invention is to have the corresponding resilient contacts integrally formed with the housing for assuring waterproofing thereof. As noted, in the conventional connector the resilient contacts are required to be inserted or assembled into the corresponding passageways in the housing, thus tending to be in an inferior waterproofing state. Differently, in the invention the resilient contacts 120 are integrally formed with the housing 130 with superior waterproofing performance. Understandably, the cable assembly 10 is used with a wearable device as disclosed in the aforementioned patents, thus tending to be in a humid circumstance. Accordingly, the waterproofing function is much desired. The reason why the invention may have resilient contacts via the insert-molding process, is to provide the transverse groove 134, wherein a tool is inserted to abut against the contacts 120, to allow the originally straight type contact (as shown in FIGS. 3, 10(A), 10(C) and 11) to be backwardly bent to form the U-shaped middle section 126 (as shown in FIGS. 2(A), 4(A), 4(B) and 10(B)). Notably, the contacts 120 are originally linked to a carrier 123 in a straight manner without backward bending for insert-molding within the housing 130. After insert-molding, the carrier 123 is removed from the contacts 120 to have the wires 22 soldered upon the soldering sections 122 of the contacts 120. Notably, in this embodiment, the soldering section 122 is downward exposed for soldering to the corresponding wire 22 while the lying U-shaped middle section 126 is upwardly exposed to allow the contacting section 124 mateable with the complementary connector in the cradle (not shown) wearable on the human arm. Notably, in the conventional design, the connector is mounted upon a printed circuit board which is enclosed within a case for grasping and linked to the wires of the cable assembly, wherein the resistor is mounted upon the printed circuit board. In this invention, the resistor is directly soldered upon the contact tails, thus being unnecessary to provide the printed circuit board. Understandably, in this embodiment the housing 130 is unitary so as to assure the superior waterproofing performance while alternately the terminal module including the contacts integrally formed within an insulator, may be discrete from and assembled to the remaining housing for easing manufacturing.

The sensor sub-assembly 200 includes a T-shaped overmolded insulative housing 202 receiving an LED (Light Emitting Diode) enclosed within the LED housing 215 with the corresponding contacts 212 mechanically and electrically connected to the corresponding wires 22, and a PD (Photo Diode) 220 enclosed within the PD housing 225 with the corresponding contacts 222 electrically and mechanically connected to the corresponding wire 22. Notably, the housing 202 has an LED cavity 204 receiving the LED housing 215 and the LED lens cover 240 atop the LED housing 215 to, and a PD cavity 206 receiving the PD housing 225 and the PD lens cover 250 atop the PD housing 225. A transverse slot 260 communicates with both the LED housing 215 and the PD housing 225 and is filled with the silicon after both the LED housing 215 and the PD housing 225 are assembled within the housing 202. The housing 202 further unitarily forms a pair of features/projections 270 for locating consideration.

Compared with the conventional design, the sensor sub-assembly 200 is equipped with the LED and the PD without involvement of the FPC (Flexible Printed Circuit) in a robust arrangement.

As shown in FIGS. 16(A)-22, a cable connector assembly 100 includes a contact module 10 sandwiched between an upper cover 60 and a lower cover 70 in the vertical direction. The contact module 10 includes a plurality of contacts 20 integrally formed within an insulator 40 via an insert-molding process. Each contact 20 includes a lower stationary horizontal section 22 and an upper deflectable/resilient curved contacting section 24 linked by a bight 26 therebetween. The horizontal section 22 is divided into a front region 28 and a rear region 30. A lance 32 is stamped out from the front region 28 to form an opening 34 therein corresponding. A tab 36 is located at the free end of the contacting section 24. The insulator 40 forms an exposed curved mating port 42 with a plurality of ribs 44 thereon. The contacting sections 24 are exposed upon the mating port 42 and separated from one another via the ribs 44. Notably, the opening 34 is filled with the material of the insulator 40, and the lance 32 is embedded within the insulator 40. The insulator 40 forms a crossbar 46 at a rear portion.

Figure 20A:
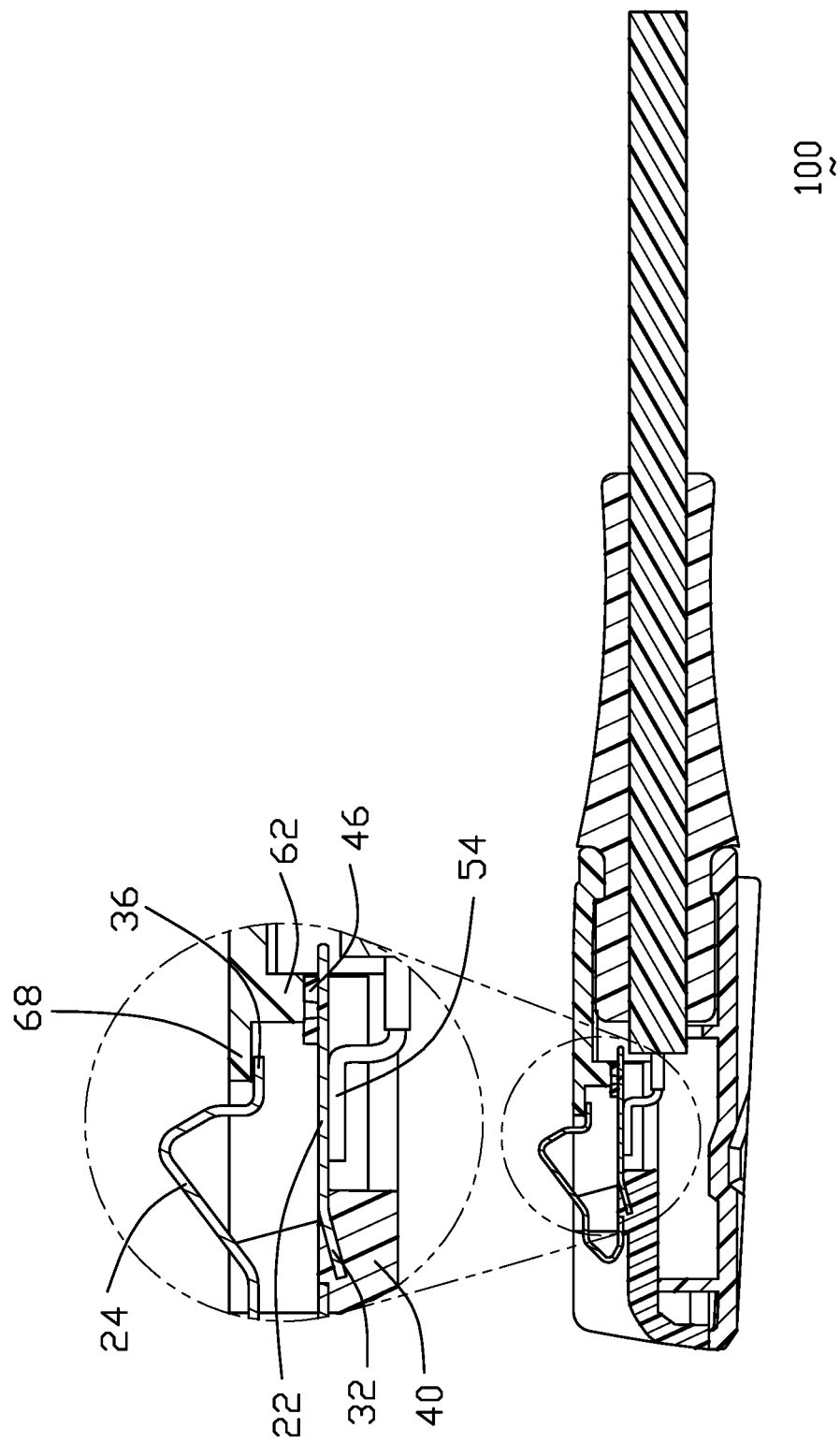
FIG. 20(A) is a cross-sectional view of the cable connector assembly of FIG. 16(A) along line 20-20.
Figure 20B:
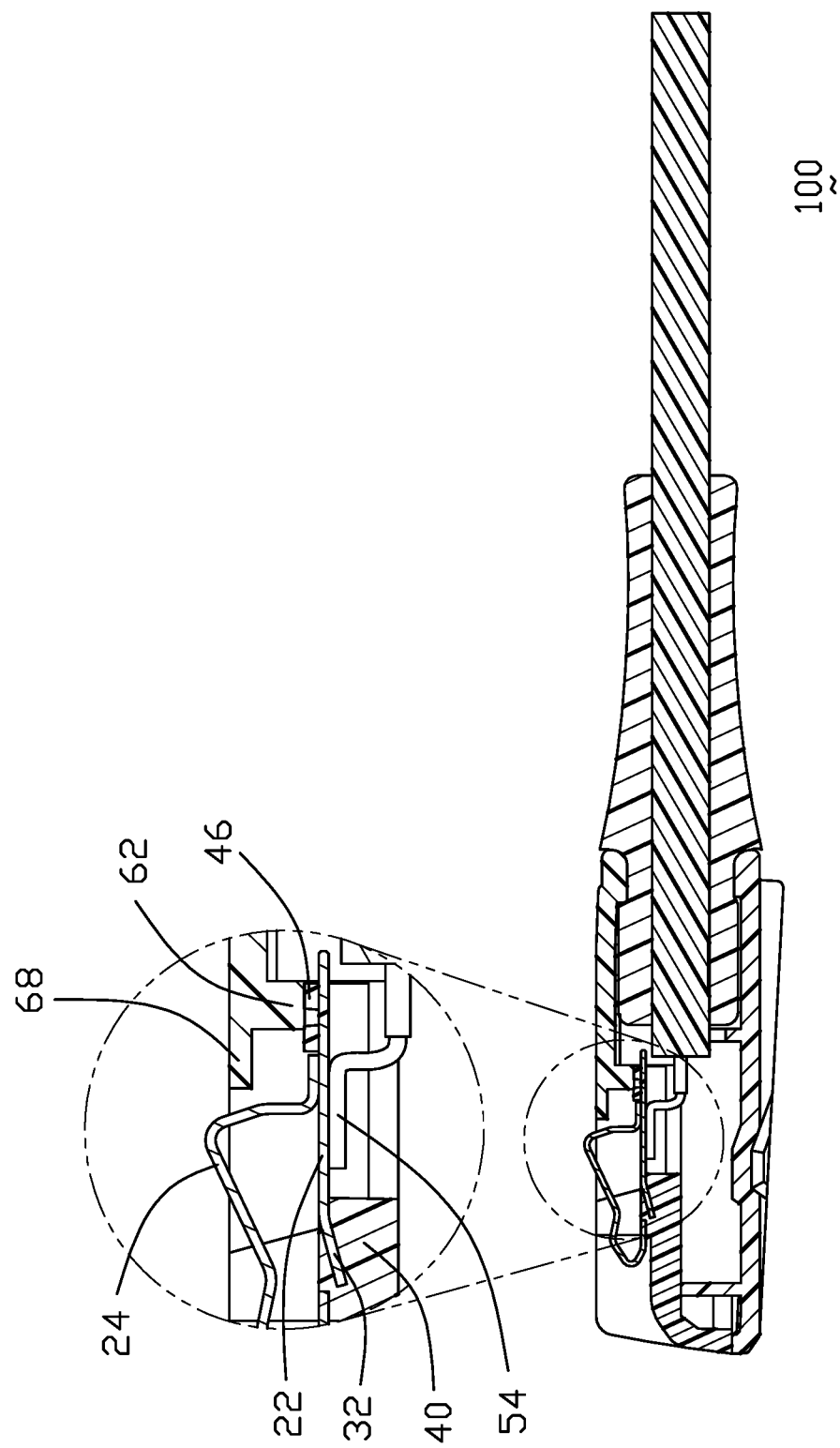
FIG. 20(B) is a cross-sectional view of the cable connector assembly of FIG. 20(A) wherein the contact is deflected during mating.

A cable 50 is located behind the contact module 10 and includes a strain relief 52 disposed in the corresponding cavities 61, 71 formed by the upper cover 60 and the lower cover 70. The upper cover 60 forms a transverse bar 62 abutting against the crossbar 46 in the vertical direction. The upper cover 60 further forms at each lateral side a step structure 64 to downwardly press the corresponding lateral side region of the contact module 10. Therefore, the contact module 10 can not move upwardly due to the step structure 64 and the transverse bar 62. Similarly, an upward structure 72 is formed on an inner surface of the lower cover 70 to upwardly support an underside of the contact module 10. Therefore, the contact module 10 can be stably retained between the upper cover 60 and the lower cover 70. Understandably, the contact 20 originally extends along the front-to-back direction when the contact module 10 is made via the insert-molding process, and the contacting section 24 is backwardly folded via the bight 26 after the contact module 10 is formed to be in a deflectable manner in the vertical direction perpendicular to the front-to-back direction. The tab 36 is downwardly pressed by the flange 68 of the upper cover 60 in a preloaded manner. As shown in FIGS. 20(A) and 20(B), even though the tab 36 is spaced from the horizontal section 22 of the corresponding contact 20 in the vertical direction when the connector assembly 100 is un-mated, such a tab 36 is downwardly moved to contact an upper side of the horizontal section 22 of the corresponding contact 20 during mating so as to result in another/shorter circuit path in addition to the original one via the bight 26 for superior signal transmission.

Figure 21A:
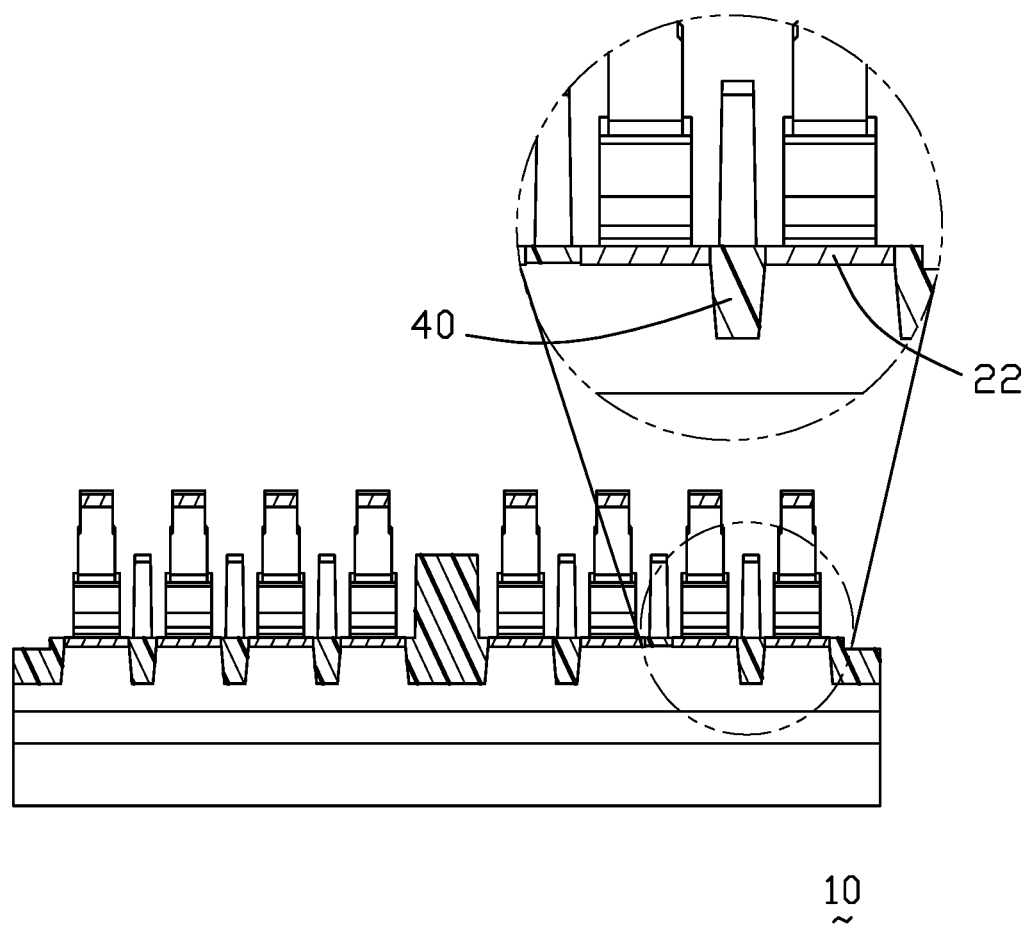
FIG. 21(A) is a cross-sectional view of the cable connector assembly of FIG. 1(A) along line 21A-21A.
Figure 21B:
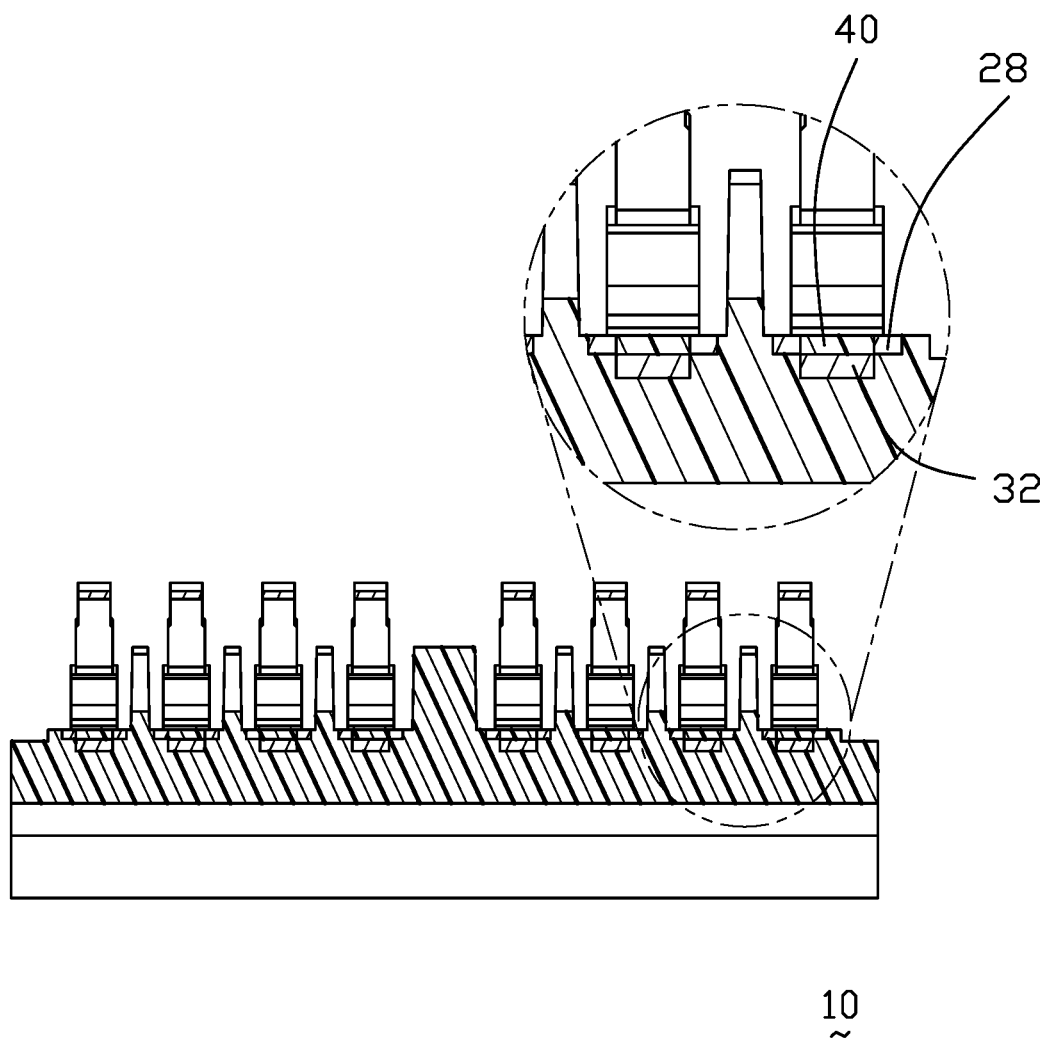
FIG. 21(B) is a cross-sectional view of the cable connector assembly of FIG. 1(A) along line 21B-21B.
Figure 22:
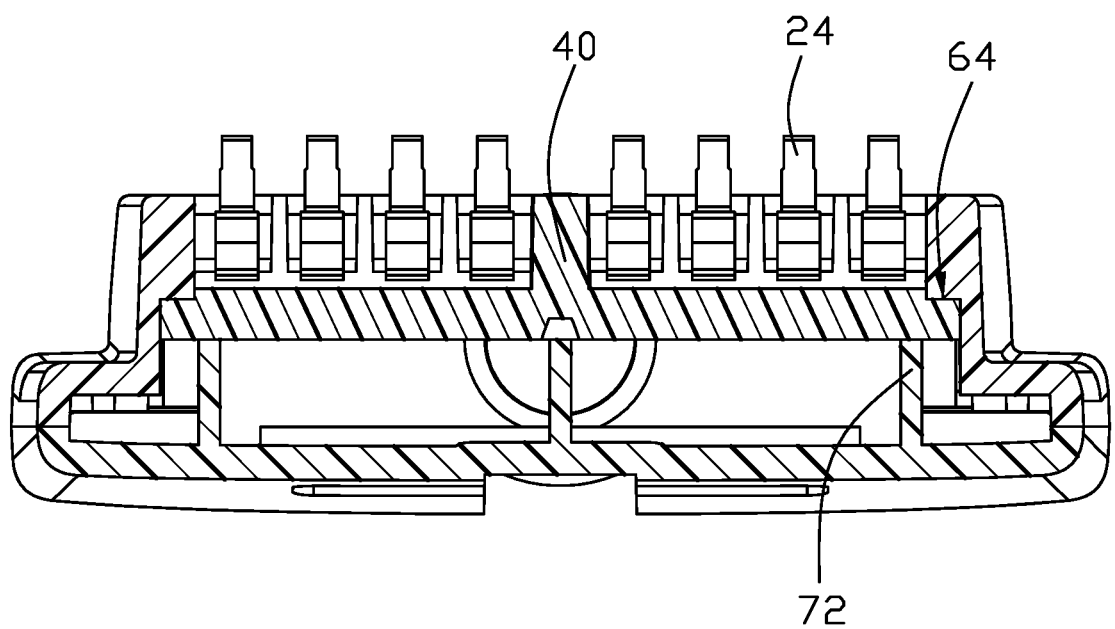
FIG. 22 is a cross-sectional view of the cable connector assembly of FIG. 1(A) along line 22-22.

The upper cover 60 forms a pair of vertical side walls 66 while the insulator 40 of the contact module 10 forms a vertical center wall 48 having the similar configuration with the vertical side walls 66 so as to form two areas in which the contacts 20 are disposed with equal amounts. The cable 50 includes a plurality of wires 54 respectively soldered upon undersides of the rear regions 30 of the corresponding contacts 20. Notably, FIG. 21(A) shows the upper side of the horizontal section 22 is essentially upwardly exposed to the exterior except the lance 32 which is hidden under the opening 34 filled by the insulator 40, While a preferred embodiment in accordance with the present disclosure has been shown and described, equivalent modifications and changes known to persons skilled in the art according to the spirit of the present disclosure are considered within the scope of the present disclosure as described in the appended claims.

What is claimed is:

1. A cable connector assembly comprising:
a contact module including a plurality of contacts integrally formed within an insulator via an insert-molding process, each of said contacts including a horizontal section extending along a front-to-back direction with two opposite top and bottom sides exposed to an exterior, a resilient curved contacting section spaced from the horizontal section in a vertical direction perpendicular to the front-to-back direction, and a bight linked therebetween;
a cable located behind the contact module and including a plurality of wires mechanically and electrically connected to the bottom sides of the horizontal sections of the corresponding contacts; and
an upper cover and a lower cover commonly sandwiching the contact module therebetween in the vertical direction; wherein the contact module forms a mating port exposed to the exterior both forwardly in the front-to-back direction and upwardly in the vertical direction;
in each contact, a lance is stamped out of the horizontal section to form a corresponding opening, and said lance is embedded within the insulator and the opening is filled with material of the insulator; and
the upper cover forms a front flange and the contact includes a tab at a free end of the contacting section pressed downwardly by the flange in a preloaded manner when the connector assembly is not mated.

2. The cable connector assembly as claimed in claim 1, wherein the insulator further includes a crossbar downwardly extending in a transverse direction perpendicular to both the front-to-back direction and the vertical direction, and pressing the upper side of the horizontal section.

3. The cable connector assembly as claimed in claim 2, wherein the upper cover forms a transverse bar downwardly pressing the crossbar of the insulator in the vertical direction.

4. The cable connector assembly as claimed in claim 1, wherein the tab is downwardly pressed to contact the top side of the horizontal section of the corresponding contact when the connector assembly is mated.

5. The cable connector assembly as claimed in claim 1, wherein the upper cover forms step structure downwardly pressing the insulator of the contact module.

6. The cable connector assembly as claimed in claim 5, wherein an upward structure is formed on an interior surface of the lower cover to upwardly press the insulator of the contact module so as to cooperate with the step structure of the upper cover to commonly sandwich the insulator of the contact module therebetween in the vertical direction.

7. The cable connector assembly as claimed in claim 1, wherein the insulator forms a vertical center wall, and the upper cover forms a pair of vertical side walls located by two sides of and having a similar configuration of to the middle center wall so as to form two contacting areas.

8. The cable connector assembly as claimed in claim 1, wherein the curved contacting section is formed after the contact is molded with the insulator.

9. The cable connector assembly as claimed in claim 1, wherein a transverse groove extends across the insulator in a transverse direction perpendicular to both the front-to-back direction and the vertical direction.

10. A cable connector assembly comprising:
a contact module including a plurality of contacts integrally formed within an insulator via an insert-molding process, each of said contacts including a horizontal section extending along a front-to-back direction with two opposite top and bottom sides exposed to an exterior, a resilient curved contacting section spaced from the horizontal section in a vertical direction perpendicular to the front-to-back direction, and a bight linked therebetween;
a cable located behind the contact module and including a plurality of wires mechanically and electrically connected to the bottom sides of the horizontal sections of the corresponding contacts; and
an upper cover and a lower cover commonly sandwiching the contact module therebetween in the vertical direction; wherein
the contact module forms a mating port exposed to the exterior both forwardly in the front-to-back direction and upwardly in the vertical direction;

in each contact, a lance is stamped out of the horizontal section to form a corresponding opening, and said lance is embedded within the insulator and the opening is filled with material of the insulator;

the upper cover forms a step structure downwardly pressing the insulator of the contact module; and an upward structure is formed on an interior surface of the lower cover to upwardly press the insulator of the contact module so as to cooperate with the step structure of the upper cover to commonly sandwich the insulator of the contact module therebetween in the vertical direction.

11. The cable connector assembly as claimed in claim 10, wherein the curved contacting section is formed after the contact is molded with the insulator.

12. The cable connector assembly as claimed in claim 10, wherein a transverse groove extends across the insulator in a transverse direction perpendicular to both the front-to-back direction and the vertical direction.

13. A cable connector assembly comprising:

a contact module including a plurality of contacts integrally formed within an insulator via an insert-molding process, each of said contacts including a horizontal section extending along a front-to-back direction with two opposite top and bottom sides exposed to an exterior, a resilient curved contacting section spaced from the horizontal section in a vertical direction perpendicular to the front-to-back direction, and a bight linked therebetween;

a cable located behind the contact module and including a plurality of wires mechanically and electrically connected to the bottom sides of the horizontal sections of the corresponding contacts; and an upper cover and a lower cover commonly sandwiching the contact module therebetween in the vertical direction; wherein the contact module forms a mating port exposed to the exterior both forwardly in the front-to-back direction and upwardly in the vertical direction;

in each contact, a lance is stamped out of the horizontal section to form a corresponding opening, and said lance is embedded within the insulator and the opening is filled with material of the insulator; and the insulator forms a vertical center wall, and the upper cover forms a pair of vertical side walls located by two sides of and having a similar configuration to the center wall so as to form two contacting areas.

14. The cable connector assembly as claimed in claim 13, wherein the curved contacting section is formed after the contact is molded with the insulator.

15. The cable connector assembly as claimed in claim 13, wherein a transverse groove extends across the insulator in a transverse direction perpendicular to both the front-to-back direction and the vertical direction.

\* \* \* \* \*